(12) United States Patent
Nozulak et al.

(10) Patent No.: US 7,786,155 B2
(45) Date of Patent: Aug. 31, 2010

(54) ORGANIC COMPOUNDS

(75) Inventors: Joachim Nozulak, Heitersheim (DE); David Orain, Hesingue (FR)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 12/251,650

(22) Filed: Oct. 15, 2008

(65) Prior Publication Data
US 2009/0099244 A1 Apr. 16, 2009

(30) Foreign Application Priority Data
Oct. 16, 2007 (EP) .................................. 07118616

(51) Int. Cl.
*A61K 31/422* (2006.01)
*A61K 31/4164* (2006.01)
*C07D 261/02* (2006.01)
*C07D 233/04* (2006.01)

(52) U.S. Cl. ..................... 514/378; 514/396; 548/247; 548/300.1

(58) Field of Classification Search .................. 514/378, 514/396; 548/247, 300.1
See application file for complete search history.

(56) References Cited

U.S. PATENT DOCUMENTS

| 5,270,317 A | 12/1993 | Bernhart et al. |
|---|---|---|
| 2005/0070534 A1 | 3/2005 | Carruthers et al. |
| 2005/0203156 A1 | 9/2005 | Olson et al. |
| 2007/0027199 A1 | 2/2007 | Malamas et al. |
| 2009/0099243 A1 | 4/2009 | Nozulak et al. |

FOREIGN PATENT DOCUMENTS

| DE | 198 16 929 A1 | 10/1999 |
|---|---|---|
| EP | 0 640 594 A1 | 3/1995 |
| WO | WO 91/14679 A1 | 10/1991 |
| WO | WO 97/31910 A1 | 9/1997 |
| WO | WO 01/00206 A1 | 1/2001 |
| WO | WO 2004/058727 A1 | 7/2004 |
| WO | WO 2005/114201 A1 | 12/2005 |
| WO | WO 2006/065277 A2 | 6/2006 |
| WO | WO 2006/136553 A1 | 12/2006 |
| WO | WO 2007/053436 A1 | 5/2007 |
| WO | WO 2007/087717 A1 | 8/2007 |

OTHER PUBLICATIONS

Mimi L. Quan et al., "Imidazolinones as Nonpeptide Angiotensin II Receptor Antagonists", Bioorganic & Medicinal Chemistry Letters, vol. 4 No. 12 (1994), pp. 1527-1530.
Claude A. Bernhart et al., "A new series of imidazolones: highly specific and potent nonpeptide AT1 angotensin II receptor antagonists", J. Med. Chem., vol. 36, No. 22 (1993), pp. 3371-3380.
Alka Kurup et al., "Comparative QSAR: Angiotensin II Antagonists", Chem. Rev., vol. 101, No. 9 (2001), pp. 2727-2750.
XP002471723, Database Registry STN International, (search results printed 2008), 30 pgs.
Joachim Nozulak, USPTO Office Action, U.S. Appl. No. 12/251,645, Oct. 1, 2009, 8 pgs.
Pascal Bonaventure et al., "Characterization of N-(1-Acetyl-2,3-dihydro-1H-indol-6-yl)-3-(3-cyano-phenyl)-N-[1-(2-cyclopentyl-ethyl)-piperidin-4yl]-acrylamide (JNJ-5207787), a Small Molecule Antagonist of the Neuropeptide Y Y2 Receptor", The Journal of Pharmacology and Experimental Therapeutics, vol. 308, No. 3 (2004), pp. 1130-1137.
Jill A. Jablonowski et al., "Novel non-peptidic neuropeptide Y Y2 receptor antagonists", Bioorganic & Medicinal Chemistry Letters, vol. 14 (2004), pp. 1239-1242.
Charles J. Andres et al., "Differentially Functionalized Diamines as Novel Ligands for the NPY2 Receptor", Bioorganic & Medicinal Chemistry Letters, vol. 13 (2003), pp. 2883-2885.
Joachim Nozulak, U.S. PTO Notice of Allowance, U.S. Appl. No. 12/251,645, May 12, 2010, 8 pgs.

*Primary Examiner*—Kamal A Saeed
*Assistant Examiner*—Samantha L Shterengarts
(74) *Attorney, Agent, or Firm*—Paul D. Strain, Esq.; Fanelli Strain & Haag PLLC

(57) ABSTRACT

The invention relates to compound of the formula I

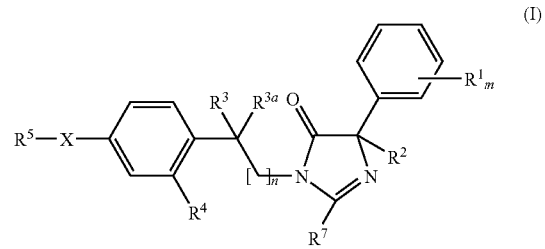

wherein the substituents are as defined in the specification; in free base form or in acid addition salt form; to its preparation, to its use as medicament and to medicaments comprising it.

6 Claims, No Drawings

ORGANIC COMPOUNDS

This application claims benefit under 35 U.S.C. §119(a)-(d) or (f) or 365(b) of EP Application No. 07118616.7, filed Oct. 16, 2007, the content of which is incorporated herein by reference in its entirety.

The present invention relates to heterocyclic compounds, to their preparation, to their use as medicaments and to medicaments comprising them.

In a first aspect, the invention relates to a compound of the formula I

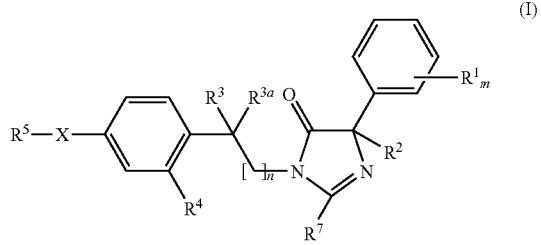

wherein
$R^3$ and $R^{3a}$ together represent oxo (=O) or
$R^3$ represents hydrogen and $R^{3a}$ represents hydroxy or
$R^3$ represents hydrogen and $R^{3a}$ represents hydrogen
and
X represents —C(O)—NR$^6$—; —NR$^6$—C(O)—, —NR$^6$—C(O)—NR$^6$—;
n represents 0, 1 or 2;
m represents 0, 1, 2 or 3;
$R^1$ represents hydrogen or a substituent different from hydrogen
$R^2$ represents represents an optionally substituted aryl group, an optionally substituted cycloalkyl group, an optionally substituted heteroaryl group, an optionally substituted heterocyclyl group; an optionally substituted alkyl group;
$R^4$ represents hydrogen or a substituent different from hydrogen
$R^5$ represents represents an optionally substituted aryl group, an optionally substituted cycloalkyl group, an optionally substituted heteroaryl group, an optionally substituted heterocyclyl group; an optionally substituted alkyl group;
$R^6$ represents hydrogen, alkyl, cycloalkyl;
$R^7$ represents H, an optionally substituted aryl group, an optionally substituted cycloalkyl group, an optionally substituted alkyl group;
and provided if n represents 0, $R^{3a}$ does not represent hydroxy;
in free base form or in acid addition salt form.

The invention may be more fully appreciated by reference to the following description, including the following glossary of terms and the concluding examples. For the sake of brevity, the disclosures of the publications cited in this specification are herein incorporated by reference. As used herein, the terms "including", "containing" and "comprising" are used herein in their open, non-limiting sense.

Any formula given herein is intended to represent compounds having structures depicted by the structural formula as well as certain variations or forms. In particular, compounds of any formula given herein may have asymmetric centers and therefore exist in different enantiomeric forms. If at least one asymmetrical carbon atom is present in a compound of the formula I, such a compound may exist in optically active form or in the form of a mixture of optical isomers, e.g. in the form of a racemic mixture. All optical isomers and their mixtures, including the racemic mixtures, are part of the present invention. Thus, any given formula given herein is intended to represents a racemate, one or more enantiomeric forms, one or more diastereomeric forms, one or more atropisomeric forms, and mixtures thereof. Furthermore, certain structures may exist as geometric isomers (i.e. cis and trans isomers), as tautomers, or as atropisomers. Additionally, any formula given herein is intended to represent hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^2$H, $^3$H, $^{11}$C, $^{13}$C, $^{14}$C, $^{15}$N, $^{18}$F $^{31}$P, $^{32}$P, $^{35}$S, $^{38}$Cl, $^{125}$J respectively. Various isotopically labeled compounds of the present invention, for example those into which radioactive isotopes such as $^3$H, $^{13}$C, and $^{14}$C are incorporated. Such isotopically labeled compounds are useful in metabolic studies (preferably with $^{14}$C), reaction kinetic studies (with, for example $^2$H or $^3$H), detection or imaging techniques [such as positron emission tomography (PET) or single-photon emission computed tomography (SPECT) including drug or substrate tissue distribution assays, or in radioactive treatment of patients. In particular, an $^{18}$F or labeled compound may be particularly preferred for PET or SPECT studies. Further, substitution with heavier isotopes such as deuterium (i.e., $^2$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula.

The acid addition salt of compounds of formula I are preferably pharmaceutically acceptable salts. Such salts are known in the field.

The following-general definitions shall apply in this specification, unless otherwise specified:

Halogen (or halo) denotes fluorine, bromine, chlorine or iodine, preferably fluorine, chlorine.

The term "Alkyl" refers to a straight-chain or branched-chain alkyl group, preferably represents a straight-chain or branched-chain $C_{1-12}$alkyl, particularly preferably represents a straight-chain or branched-chain $C_{1-6}$alkyl; for example, methyl, ethyl, n- or iso-propyl, n-, iso-, sec- or tert-butyl, n-pentyl, n-hexyl, n-heptyl, n-octyl, n-nonyl, n-decyl, n-undecyl, n-dodecyl, with particular preference given to methyl, ethyl, n-propyl, iso-propyl and n-butyl and iso-butyl. Alkyl may be unsubstituted or substituted. Exemplary substituents include, but are not limited to hydroxyl, alkoxy, halogen and amino. An example of a substituted alkyl is trifluoromethyl.

Further, cyclocalkyl may be a substituent to alkyl. An example of such a case is the moiety (alkyl)-cyclopropyl or alkandiyl-cycloproyl, e.g. —$CH_2$-cyclopropyl.

"Alkenyl" represents a straight-chain or branched-chain alkenyl group and may be substituted or unsubstituted, preferably $C_{2-6}$alkenyl, for example, vinyl, allyl, 1-propenyl, isopropenyl, 2-butenyl, 2-pentenyl, 2-hexenyl, etc. and preferably represents unsubstituted $C_{2-4}$ alkenyl.

Each alkyl part of "alkoxy", "alkoxyalkyl", "alkoxycarbonyl", "alkoxycarbonylalkyl" and "halogenalkyl" shall have the same meaning as described in the above-mentioned definition of "alkyl".

The term "Alkandiyl" refers to a straight-chain or branched-chain alkandiyl group bound by two different Carbon atoms to the moiety, it preferably represents a straight-chain or branched-chain $C_{1-12}$ alkandiyl, particularly preferably represents a straight-chain or branched-chain $C_{1-6}$ alkandiyl; for example, methandiyl (—$CH_2$—), 1,2-ethanediyl (—$CH_2$—$CH_2$—), 1,1-ethanediyl ((—CH($CH_3$)—), 1,1-, 1 2-, 1,3-propanediyl and 1,1-, 1,2-, 1,3-, 1,4-butanediyl, with particular preference given to methandiyl, 1,1-ethanediyl, 1,2-ethanediyl, 1,3-propanediyl, 1,4-butanediyl.

The term "Alkendiyl" refers to a straight-chain or branched-chain alkendiyl group bound by two different Carbon atoms to the molecule, it preferably represents a straight-chain or branched-chain $C_{2-6}$ alkandiyl; for example, —CH=CH—, —CH=C($CH_3$)—, —CH=CH—$CH_2$—, —C($CH_3$)=CH—$CH_2$—, —CH=C($CH_3$)—$CH_2$—, —CH=CH—C($CH_3$)H—, —CH=CH—CH=CH—, —C($CH_3$)=CH—CH=CH—, —CH=C($CH_3$)—CH=CH—, with particular preference given to —CH=CH—$CH_2$—, —CH=CH—CH=CH—. Alkendiyl may be substituted or unsubstituted The term "cycloalkyl" refers to a saturated or partially saturated, monocyclic, fused polycyclic, or Spiro polycyclic, carbocycle having from 3 to 12 ring atoms per carbocycle. Illustrative examples of cycloalkyl groups include the following moieties: cyclopropyl, cyclobutyl, cyclpentyl and cylclohexyl.

The term "aryl" is known in the field. Aryl is preferably naphthyl or phenyl, in particular phenyl.

The term "heterocyclyl" refers to a saturated or partly saturated ring system containing at least one hetero atom. Preferably, heterocyclyl groups consist of 3 to 11 ring atoms of which 1-3 ring atoms are hetero atoms. Heterocycles may be present as a single ring system or as bicyclic or tricyclic ring systems; preferably as single ring system or as benz-annelated ring system. Bicyclic or tricyclic ring systems may be formed by annelation of two or more rings, by a bridging atom, e.g. oxygen, sulfur, nitrogen or by a bridging group, e.g. alkandediyl or alkenediyl. A Heterocycle may be substituted by one or more substituents selected from the group consisting of Oxo (=O), halogen, nitro, cyano, alkyl, alkandiyl, alkenediyl, alkoxy, alkoxyalkyl, alkoxycarbonyl, alkoxycarbonylalkyl, halogenalkyl, aryl, aryloxy, arylalkyl.

The term "heteroaryl" refers to an aromatic ring system containing at least one hetero atom. Preferably, heteroaryl groups consist of 3 to 11 ring atoms of which 1-3 ring atoms are hetero atoms. Heteroary groups may be present as a single ring system or as bicyclic or tricyclic ring systems; preferably as single ring system or as benz-annelated ring system. Bicyclic or tricyclic ring systems may be formed by annelation of two or more rings. A Heterocycle may be substituted by one or more substituents selected from the group consisting of Oxo (=O), halogen, nitro, cyano, alkyl, alkandiyl, alkenediyl, alkoxy, alkoxyalkyl, alkoxycarbonyl, alkoxycarbonylalkyl, halogenalkyl, aryl, aryloxy, arylalkyl. Examples of heterocyclyl and heteroaryl groups include: pyrrole, pyrroline, pyrrolidine, pyrazole, pyrazoline, pyrazolidine, imidazole, imidazoline, imidazolidine, triazole, triazoline, triazolidine, tetrazole, furane, dihydrofurane, tetrahydrofurane, furazane (oxadiazole), dioxolane, thiophene, dihydrothiophene, tetrahydrothiophene, oxazole, oxazoline, oxazolidine, isoxazole, isoxazoline, isoxazolidine, thiazole, thiazoline, thiazlolidine, isothiazole, istothiazoline, isothiazolidine, thiadiazole, thiadiazoline, thiadiazolidine, pyridine, piperidine, pyridazine, pyrazine, piperazine, triazine, pyrane, tetrahydropyrane, thiopyrane, tetrahydrothiopyrane, oxazine, thiazine, dioxine, morpholine, purine, pterine, and the corresponding benz-annelated heterocycles, e.g. indole, isoindole, cumarine, cumaronecinoline, isochinoline, cinnoline.

The term "arylalkyl" refers to an aryl group bound to the molecule via an alkyl group, such as a methyl or ethyl group, preferably phenethyl or benzyl, in particular benzyl. Similarly, cycloalkylalkyl and heterocyclyl represents a cycloalkyl group bound to the molecule via an alkyl group or a heterocyclyl group bound to the molecule via an alkyl group.

Carbon containing groups, moieties or molecules contain 1 to 8, preferably 1 to 6, more preferably 1 to 4, most preferably 1 or 2, carbon atoms. Any non-cyclic carbon containing group or moiety with more than 1 carbon atom is straight-chain or branched.

Hetero atoms are atoms other than carbon and hydrogen, preferably nitrogen (N), oxygen (O) or sulfur (S).

Halogen-substituted groups and moieties, such as alkyl substituted by halogen(halogenalkyl) can be mono-, poly- or per-halogenated.

In preferred embodiments, which are preferred independently, collectively or in any combination or sub-combination, the invention relates to a compound of the formula I, in free base form or in acid addition salt form, wherein the substituents are as defined herein.

In an advantageous embodiment, the invention relates to a compound of formula IA

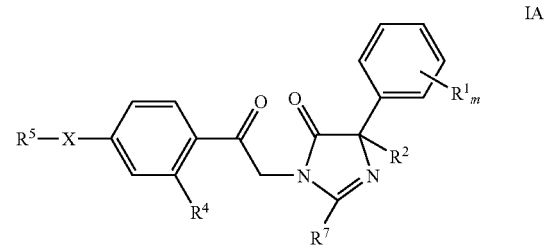

IA wherein the substituents are as defined for a compound of formula I.

In a further advantageous embodiment, the invention relates to a compound of formula IB

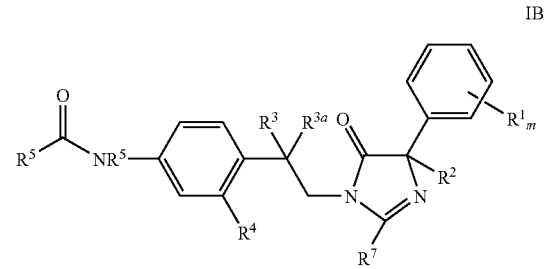

IB wherein the substituents are as defined for a compound of formula I.

In a further advantageous embodiment, the invention relates to a compound of formula IC

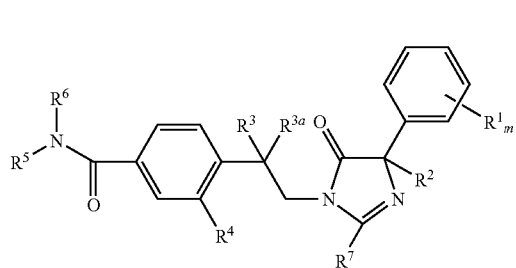

IC wherein the substituents are as defined for a compound of formula I.

In a further advantageous embodiment, the invention relates to a compound of formula ID

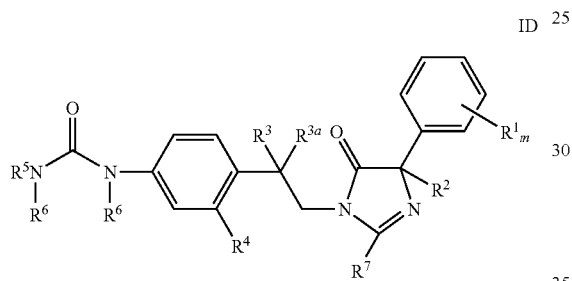

ID wherein the substituents are as defined for a compound of formula I.

In especially preferred embodiments, the invention relates to one or more than one of the compounds of the formula I mentioned in the Examples hereinafter, in free base form or in acid addition salt form.

$R^1$ preferably represents hydrogen, halogen, cyano, nitro, $(C_{1-8})$alkyl, $(C_{1-8})$alkyl substituted by halogen, $(C_{3-8})$cycloalkyl, $(C_{3-8})$cycloalkyl$(C_{1-8})$alkyl, $(C_{3-8})$cycloalkoxy, $(C_{3-8})$cycloalkoxy$(C_{1-8})$alkyl, $(C_{3-8})$cycloalkyl$(C_{1-8})$alkoxy, $(C_{3-8})$cycloalkoxy$(C_{1-8})$alkoxy, aryl, aryl$(C_{1-8})$alkyl, aryloxy, aryloxy$(C_{1-8})$alkyl, aryl$(C_{1-8})$alkoxy, aryloxy$(C_{1-8})$alkoxy, carboxy, carbamyl, hydroxy, $(C_{1-8})$alkoxy, $(C_{1-8})$alkoxy$(C_{1-8})$alkoxy, $(C_{1-8})$alkoxy substituted by halogen, $(C_{1-8})$alkoxy$(C_{1-8})$alkyl, $(C_{1-8})$alkylthio, $(C_{1-8})$alkylthio$(C_{1-8})$alkyl, $(C_{1-8})$alkylsulfinyl, $(C_{1-8})$alkylsulfinyl$(C_{1-8})$alkyl, $(C_{1-8})$alkylsulfonyl, $(C_{1-8})$alkylsulfonyl$(C_{1-8})$alkyl, amino, $(C_{1-8})$alkylamino, di$(C_{1-8})$alkylamino with two identical or different $(C_{1-8})$alkyl moieties, amino$(C_{1-8})$alkyl, $(C_{1-8})$alkylamino$(C_{1-8})$alkyl, di$(C_{1-8})$alkylamino$(C_{1-8})$alkyl with two identical or different $(C_{1-8})$alkyl moieties in the di$(C_{1-8})$alkylamino moiety, amino, $(C_{1-8})$alkoxy, $(C_{1-8})$alkylamino $(C_{1-8})$alkoxy, di$(C_{1-8})$alkylamino $(C_{1-8})$alkoxy with two identical or different $(C_{1-8})$alkyl moieties, aminosulfonyl, $(C_{1-8})$alkylaminosulfonyl, di$(C_{1-8})$alkylaminosulfonyl with two identical or different $(C_{1-8})$alkyl moieties, formyl, $(C_{1-8})$alkylcarbonyl, formyloxy, $(C_{1-8})$alkylcarbonyloxy, formyl $(C_{1-8})$alkyl, $(C_{1-8})$alkylcarbonyl$(C_{1-8})$alkyl, formyl(Cl-s)alkoxy, $(C_{1-8})$alkylcarbonyl$(C_{1-8})$alkoxy, $(C_{1-8})$ alkoxycarbonyl, $(C_{1-8})$alkoxycarbonyloxy, $(C_{1-8})$ alkoxycarbonyl$(C_{1-8})$alkyl and $(C_{1-8})$alkoxycarbonyl $(C_{1-8})$alkoxy.

$R^1$ particular preferably represents hydrogen, halogen, cyano, $(C_{1-8})$alkyl, $(C_{1-8})$alkyl substituted by halogen, $(C_{1-8})$ alkoxy, amino, $(C_{1-8})$alkylamino and di$(C_{1-8})$alkylamino with two identical or different $(C_{1-8})$alkyl moieties;

$R^1$ very particular preferably represents hydrogen, fluoro, chloro, cyano, methyl, ethyl, trifluoromethyl, methoxy.

$R^1$ further very particular preferably represents hydrogen.

$R^2$ preferably represents an aryl group or a $(C_3-C_8)$cycloalkyl group or a heterocyclyl group with 3 to 8 ring atoms or a heteroaryl group with 3 to 8 ring atoms or a $(C_1-C_8)$alkyl group;

wherein said aryl group, $(C_3-C_8)$cycloalkyl group, heteroaryl group, heterocyclyl group group is unsubstituted, mono-substituted, di-substituted or tetra-substituted, the optional substituent(s) being independently selected from the group consisting of halogen, cyano, nitro, carboxy, carbamyl, hydroxy, $(C_{1-8})$alkyl, $(C_{1-8})$ alkyl substituted by halogen, $(C_{3-8})$cycloalkyl, $(C_{3-8})$ cycloalkyl$(C_{1-8})$alkyl, (C3s)cycloalkoxy, $(C_{3-8})$cycloalkoxy$(C_{1-8})$alkyl, $(C_{3-8})$cycloalkyl$(C_{1-8})$alkoxy, $(C_{3-8})$cycloalkoxy$(C_{1-8})$alkoxy, aryl, aryl$(C_{1-8})$alkyl, aryloxy, aryloxy$(C_{1-8})$alkyl, aryl$(C_{1-8})$alkoxy, aryloxy $(C_{1-8})$alkoxy, $(C_{1-8})$alkoxy, $(C_{1-8})$alkoxy$(C_{1-8})$alkoxy, $(C_{1-8})$alkoxy substituted by halogen, $(C_{1-8})$alkoxy$(C_{1-8})$ alkyl, $(C_{1-8})$alkylthio, $(C_{1-8})$alkylthio$(C_{1-8})$alkyl, $(C_{1-8})$ alkylsulfinyl, $(C_{1-8})$alkylsulfinyl$(C_{1-8})$alkyl, $(C_{1-8})$ alkylsulfonyl, $(C_{1-8})$alkylsulfonyl$(C_{1-8})$alkyl, amino, $(C_{1-8})$alkylamino, di$(C_{1-8})$alkylamino with two identical or different $(C_{1-8})$alkyl moieties, amino$(C_{1-8})$alkyl, $(C_{1-8})$alkylamino$(C_{1-8})$alkyl, di$(C_{1-8})$alkylamino$(C_{1-8})$ alkyl with two identical or different $(C_{1-8})$alkyl moieties in the di$(C_{1-8})$alkylamino moiety, amino$(C_{1-8})$alkoxy, $(C_{1-8})$alkylamino$(C_{1-8})$alkoxy, di$(C_{1-8})$alkylamino $(C_{1-8})$alkoxy with two identical or different $(C_{1-8})$alkyl moieties, formyl, $(C_{1-8})$alkylcarbonyl, formyloxy, $(C_{1-8})$alkylcarbonyloxy, formyl$(C_{1-8})$alkyl, $(C_{1-8})$alkylcarbonyl$(C_{1-8})$alkyl, formyl$(C_{1-8})$alkoxy, $(C_{1-8})$alkylcarbonyl$(C_{1-8})$alkoxy, $(C_{1-8})$alkoxycarbonyl, $(C_{1-8})$ alkoxycarbonyloxy, $(C_{1-8})$alkoxycarbonyl$(C_{1-8})$alkyl, $(C_{1-8})$alkoxycarbonyl$(C_{1-8})$alkoxy, —OCH$_2$O—, —C(═O)OCH$_2$—, —CH$_2$OC(═O)— and —CH═CHCH═CH—, the four last-mentioned optional substituents in each case being attached to two adjacent ring carbon atoms of the said moiety and wherein said $(C_{1-8})$alkyl group is unsubstituted or mono-, di-, tri or tetra-substituted, the optional substituent(s) on the said $(C_{1-8})$alkyl moiety being independently selected from the group consisting of halogen, cyano, oxo, nitro, amino, $(C_{1-8})$alkoxy, $(C_{1-8})$alkoxy$(C_{1-8})$alkoxy, $(C_{1-8})$ alkylthio, $(C_{1-8})$alkylsulfinyl, (Cl14) alkylsulfonyl, $(C_{1-8})$alkylcarbonyloxy, $(C_{1-8})$alkoxycarbonyl and $(C_{1-8})$alkoxycarbonyloxy, $(C_{3-8})$cycloalkyl, $(C_{3-8})$cycloalkyl$(C_{1-8})$alkyl, $(C_{3-8})$cycloalkoxy, $(C_{3-8})$cycloalkoxy$(C_{1-8})$alkyl, $(C_{3-8})$cycloalkyl$(C_{1-8})$alkoxy, $(C_{3-8})$cycloalkoxy$(C_{1-8})$alkoxy, aryl, aryl$(C_{1-8})$alkyl, aryloxy, aryloxy$(C_{1-8})$alkyl, aryl$(C_{1-8})$alkoxy, aryloxy $(C_{1-8})$alkoxy, carboxy, carbamyl, hydroxy, $(C_{1-8})$ alkoxy, $(C_{1-8})$alkoxy$(C_{1-8})$alkoxy, $(C_{1-8})$alkoxy substituted by halogen, $(C_{1-8})$alkoxy$(C_{1-8})$alkyl, $(C_{1-8})$ alkylthio, $(C_{1-8})$alkylthio$(C_{1-8})$alkyl, $(C_{1-8})$ alkylsulfinyl, $(C_{1-8})$alkylsulfinyl$(C_{1-8})$alkyl, $(C_{1-8})$ alkylsulfonyl, $(C_{1-8})$alkylsulfonyl$(C_{1-8})$alkyl, $(C_{1-8})$ alkyl-amino, di$(C_{1-8})$alkylamino with two identical or different $(C_{1-8})$alkyl moieties, amino$(C_{1-8})$alkyl, $(C_{1-8})$ alkylamino($C_{1-8}$)alkyl, di($C_{1-8}$)alkylamino($C_{1-8}$)alkyl with two identical or different ($C_{1-8}$)alkyl moieties in the di($C_{1-8}$)alkylamino moiety, amino($C_{1-8}$)alkoxy, ($C_{1-8}$)alkylamino($C_{1-8}$)alkoxy, di($C_{1-8}$)alkylamino($C_{1-8}$)alkoxy with two identical or different ($C_{1-8}$)alkyl moieties, formyl, ($C_{1-8}$)alkylcarbonyl, formyloxy, ($C_{1-8}$)alkylcarbonyloxy, formyl($C_{1-8}$)alkyl, ($C_{1-8}$)alkylcarbonyl($C_{1-8}$)alkyl, formyl($C_{1-8}$)alkoxy, ($C_{1-8}$)alkylcarbonyl($C_{1-8}$)alkoxy, ($C_{1-8}$)alkoxycarbonyl, ($C_{1-8}$)alkoxycarbonyloxy, ($C_{1-8}$)alkoxycarbonyl($C_{1-8}$)alkyl, ($C_{1-8}$)alkoxycarbonyl($C_{1-8}$)alkoxy.

$R^2$ particular preferably represents an aryl group or a ($C_3$-$C_8$) cycloalkyl group or a heteroaryl group with 5 or 6 ring atoms, or a heterocyclyl group with 5 or 6 ring atoms or a ($C_1$-$C_8$)alkyl group, which is unsubstituted or mono-, di-, tri- or tetra-substituted on the aryl group, the optional substituent(s) on said moiety being independently selected from the group, consisting of halogen, cyano, ($C_{1-8}$)alkyl, ($C_{1-8}$)alkyl substituted by halogen, nitro, ($C_{1-8}$)alkoxy, ($C_{1-8}$)alkoxy substituted by halogen, ($C_{1-8}$)alkylthio, formyloxy, ($C_{1-8}$)alkylcarbonyloxy;

which is unsubstituted or mono-, di-, tri- or tetra-substituted on the ($C_3$-$C_8$)cycloalkyl group, the optional substituent(s) on said group being independently selected from the group, consisting of halogen, cyano, oxo, amino, ($C_{1-8}$)alkyl, ($C_{1-8}$)alkyl substituted by halogen, nitro, ($C_{1-8}$)alkoxy, ($C_{1-8}$)alkoxy substituted by halogen, ($C_{1-8}$)alkylthio, formyloxy, ($C_{1-8}$)alkylcarbonyloxy;

which is unsubstituted or mono-, di-, tri- or tetra-substituted on the heteroaryl group, the optional substituent(s) on the said group being independently selected from the group, consisting of halogen, cyano, oxo, amino, ($C_{1-8}$)alkyl, ($C_{1-8}$)alkyl substituted by halogen, nitro, ($C_{1-8}$)alkoxy, ($C_{1-8}$)alkoxy substituted by halogen, ($C_{1-8}$)alkylthio, formyloxy, ($C_{1-8}$)alkylcarbonyloxy; and whereby the heterocyclylmoiety is contains 1-3 nitrogen atoms or 0-2 nitrogen and one oxygen atom;

which is unsubstituted or mono-, di-, tri- or tetra-substituted on the heterocyclyl group, the optional substituent(s) on the said group being independently selected from the group, consisting of halogen, cyano, ($C_{1-8}$)alkyl, ($C_{1-8}$)alkyl substituted by halogen, nitro, ($C_{1-8}$)alkoxy, ($C_{1-8}$)alkoxy substituted by halogen, ($C_{1-8}$)alkylthio, formyloxy, ($C_{1-8}$)alkylcarbonyloxy; and whereby the heterocyclylmoiety is contains 1-3 nitrogen atoms or 0-2 nitrogen and one oxygen atom which is unsubstituted in the ($C_1$-$C_8$)alkyl group.

$R^2$ very particular preferably represents an unsubstituted ($C_1$-$C_6$)alkyl group or phenyl.

$R^2$ very particular preferably represents an unsubstituted ($C_1$-$C_8$)alkyl group.

$R^2$ very particular preferably represents unsubstituted phenyl.

In one embodiment, $R^3$ and $R^{3a}$ together represent oxo (=O).

In one embodiment, $R^3$ represents hydrogen and $R^{3a}$ represents hydroxyl.

In one embodiment, $R^3$ represents hydrogen and $R^{3a}$ represents hydrogen.

$R^4$ preferably represents hydrogen, halogen, cyano, nitro, ($C_{1-8}$)alkyl, ($C_{1-8}$)alkyl substituted by halogen, ($C_{3-8}$)cycloalkyl, ($C_{3-8}$)cycloalkyl($C_{1-8}$)alkyl, ($C_{3-4}$)cycloalkoxy, ($C_{3-8}$)cycloalkoxy($C_{1-8}$)alkyl, ($C_{3-8}$)cycloalkyl($C_{1-8}$)alkoxy, ($C_{3-8}$)cycloalkoxy($C_{1-8}$)alkoxy, aryl, aryl($C_{1-8}$)alkyl, aryloxy, aryloxy($C_{1-8}$)alkyl, aryl($C_{1-8}$)alkoxy, aryloxy($C_{1-8}$)alkoxy, carboxy, carbamyl, hydroxy, ($C_{1-8}$)alkoxy, ($C_{1-8}$)alkoxy($C_{1-8}$)alkoxy, ($C_{1-8}$)alkoxy substituted by halogen, ($C_{1-8}$)alkoxy($C_{1-8}$)alkyl, ($C_{1-8}$)alkylthio, ($C_{1-8}$)alkylthio($C_{1-8}$)alkyl, ($C_{1-8}$)alkylsulfinyl, ($C_{1-8}$)alkylsulfinyl($C_{1-8}$)alkyl, ($C_{1-8}$)alkylsulfonyl, ($C_{1-8}$)alkylsulfonyl($C_{1-8}$)alkyl, amino, ($C_{1-8}$)alkylamino, di($C_{1-8}$)alkylamino with two identical or different ($C_{1-8}$)alkyl moieties, amino($C_{1-8}$)alkyl, ($C_{1-8}$)alkylamino($C_{1-8}$)alkyl, di($C_{1-8}$)alkylamino($C_1$)alkyl with two identical or different ($C_{1-8}$)alkyl moieties in the di($C_{1-8}$)alkylamino moiety, amino, ($C_{1-8}$)alkoxy, ($C_{1-8}$)alkylamino ($C_{1-8}$)alkoxy, di($C_{1-8}$)alkylamino ($C_{1-8}$)alkoxy with two identical or different ($C_{1-8}$)alkyl moieties, aminosulfonyl, ($C_{1-8}$)alkylaminosulfonyl, di($C_{1-8}$)alkylaminosulfonyl with two identical or different ($C_{1-8}$)alkyl moieties, formyl, ($C_{1-8}$)alkylcarbonyl, formyloxy, ($C_{1-8}$)alkylcarbonyloxy, formyl ($C_{1-8}$)alkyl, ($C_{1-8}$)alkylcarbonyl($C_{1-8}$)alkyl, formyl($C_{1-8}$)alkoxy, ($C_{1-8}$)alkylcarbonyl($C_{1-8}$)alkoxy, ($C_{1-8}$)alkoxycarbonyl, ($C_{1-8}$)alkoxycarbonyloxy, ($C_{1-8}$)alkoxycarbonyl($C_{1-8}$)alkyl and ($C_{1-8}$)alkoxycarbonyl($C_{1-8}$)alkoxy.

$R^4$ particular preferably represents hydrogen, halogen, cyano, ($C_{1-8}$)alkyl, ($C_{1-8}$)alkyl substituted by halogen, ($C_{1-8}$)alkoxy, amino, ($C_{1-8}$)alkylamino and di($C_{1-8}$)alkylamino with two identical or different ($C_{1-8}$)alkyl moieties.

$R^4$ very particular preferably represents hydrogen, fluoro, chloro, cyano, methyl, ethyl, trifluormethyl, methoxy.

$R^4$ further very particular preferably represents hydrogen.

$R^4$ further very particular preferably represents fluoro, chloro, cyano, methyl, ethyl, trifluormethyl, methoxy.

$R^5$ preferably represents an aryl group or a ($C_3$-$C_8$)cycloalkyl group or a heterocyclyl group with 3 to 8 ring atoms or a heteroaryl group with 3 to 8 ring atoms or a ($C_1$-$C_8$)alkyl group;

wherein said aryl group, ($C_3$-$C_8$)cycloalkyl group, heteroaryl group, heterocyclyl group group is unsubstituted, mono-substituted, di-substituted or tetra-substituted, the optional substituent(s) being independently selected from the group consisting of halogen, cyano, nitro, carboxy, carbamyl, hydroxy, ($C_{1-8}$)alkyl, ($C_{1-8}$)alkyl substituted by halogen, ($C_{3-8}$)cycloalkyl, ($C_{3-8}$)cycloalkyl($C_{1-8}$)alkyl, ($C_{3-8}$)cycloalkoxy, ($C_{3-8}$)cycloalkoxy($C_{1-8}$)alkyl, ($C_{3-8}$)cycloalkyl($C_{1-8}$)alkoxy, ($C_{3-8}$)cycloalkoxy($C_{1-8}$)alkoxy, aryl, aryl($C_{1-8}$)alkyl, aryloxy, aryloxy($C_{1-8}$)alkyl, aryl($C_{1-8}$)alkoxy, aryloxy($C_{1-8}$)alkoxy, ($C_{1-8}$)alkoxy, ($C_{1-8}$)alkoxy($C_{1-8}$)alkoxy, ($C_{1-8}$)alkoxy substituted by halogen, ($C_{1-8}$)alkoxy($C_{1-8}$)alkyl, ($C_{1-8}$)alkylthio, ($C_{1-8}$)alkylthio($C_{1-8}$)alkyl, ($C_{1-8}$)alkylsulfinyl, ($C_{1-8}$)alkylsulfinyl($C_{1-8}$)alkyl, ($C_{1-8}$)alkylsulfonyl, ($C_{1-8}$)alkylsulfonyl($C_{1-8}$)alkyl, amino, ($C_{1-8}$)alkylamino, di($C_{1-8}$)alkylamino with two identical or different ($C_{1-8}$)alkyl moieties, amino($C_{1-8}$)alkyl, ($C_{1-8}$)alkylamino($C_{1-8}$)alkyl, di($C_{1-8}$)alkylamino($C_{1-8}$)alkyl with two identical or different ($C_{1-8}$)alkyl moieties in the di($C_{1-8}$)alkylamino moiety, amino($C_{1-8}$)alkoxy, ($C_{1-8}$)alkylamino($C_{1-8}$)alkoxy, di($C_{1-8}$)alkylamino ($C_{1-8}$)alkoxy with two identical or different ($C_{1-8}$)alkyl moieties, formyl, ($C_{1-8}$)alkylcarbonyl, formyloxy, ($C_{1-8}$)alkylcarbonyloxy, formyl($C_{1-8}$)alkyl, ($C_{1-8}$)alkylcarbonyl($C_{1-8}$)alkyl, formyl($C_{1-8}$)alkoxy, ($C_{1-8}$)alkylcarbonyl($C_{1-8}$)alkoxy, ($C_{1-8}$)alkoxycarbonyl, ($C_{1-8}$)alkoxycarbonyloxy, ($C_{1-8}$)alkoxycarbonyl($C_{1-8}$)alkyl, ($C_{1-8}$)alkoxycarbonyl($C_{1-8}$)alkoxy, —$OCH_2O$—, —$C(=O)OCH_2$—, —$CH_2OC(=O)$— and —$CH=CHCH=CH$—, the four last-mentioned optional substituents in each case being attached to two adjacent ring carbon atoms of the said moiety and wherein said ($C_{1-8}$)alkyl group is unsubstituted or mono-, di-, tri or tetra-substituted, the optional substituent(s) on the said ($C_{1-8}$)alkyl moiety being independently selected from the group consisting of halogen, cyano, oxo, ($C_{1-8}$)alkoxy, ($C_{1-8}$)alkoxy($C_{1-8}$)alkoxy, ($C_{1-8}$)alkylthio, ($C_{1-8}$)alkylsulfinyl, ($C_{1-8}$) alkylsulfonyl, ($C_{1-8}$) alkylcarbonyloxy, ($C_{1-8}$)alkoxycarbonyl and ($C_{1-8}$) alkoxycarbonyloxy.

$R^5$ particular preferably represents an aryl group or a ($C_3$-$C_8$) cycloalkyl group or a heteroaryl group with 5 or 6 ring atoms, or a heterocyclyl group with 5 or 6 ring atoms or a ($C_1$-$C_8$)alkyl group, which is unsubstituted or mono-, di-, tri- or tetra-substituted on the aryl group, the optional substituent(s) on said moiety being independently selected from the group, consisting of halogen, cyano, ($C_{1-8}$)alkyl, ($C_{1-8}$) alkyl substituted by halogen, nitro, ($C_{1-8}$)alkoxy, ($C_{1-8}$) alkoxy substituted by halogen, ($C_{1-8}$)alkylthio, formyloxy, ($C_{1-8}$)alkylcarbonyloxy;

which is unsubstituted or mono-, di-, tri- or tetra-substituted on the ($C_3$-$C_8$)cycloalkyl group, the optional substituent(s) on said group being independently selected from the group, consisting of halogen, cyano, ($C_{1-8}$) alkyl, ($C_{1-8}$)alkyl substituted by halogen, nitro, ($C_{1-8}$) alkoxy, ($C_{1-8}$)alkoxy substituted by halogen, ($C_{1-8}$)alkylthio, formyloxy, ($C_{1-8}$)alkylcarbonyloxy;

which is unsubstituted or mono-, di-, tri- or tetra-substituted on the heteroaryl group, the optional substituent(s) on the said group being independently selected from the group, consisting of halogen, cyano, ($C_{1-8}$)alkyl, ($C_{1-8}$) alkyl substituted by halogen, nitro, ($C_{1-8}$)alkoxy, ($C_{1-8}$) alkoxy substituted by halogen, ($C_{1-8}$)alkylthio, formyloxy, ($C_{1-8}$)alkylcarbonyloxy; and whereby the heterocyclylmoiety is contains 1-3 nitrogen atoms or 0-2 nitrogen atom;

which is unsubstituted or mono-, di-, tri- or tetra-substituted on the heterocyclyl group, the optional substituent(s) on the said group being independently selected from the group, consisting of halogen, cyano, ($C_{1-8}$)alkyl, ($C_{1-8}$)alkyl substituted by halogen, nitro, ($C_{1-8}$)alkoxy, ($C_{1-8}$)alkoxy substituted by halogen, ($C_{1-8}$)alkylthio, formyloxy, ($C_{1-8}$)alkylcarbonyloxy; and whereby the heterocyclylmoiety is contains 1-3 nitrogen atoms or 0-2 nitrogen and one oxygen atom which is unsubstituted in the ($C_1$-$C_8$)alkyl group.

$R^5$ very particular preferably represents unsubstituted $C_1$-$C_6$ alkyl. $C_5$ heterocyclyl substituted by one or two $C_1$-$C_4$ alkyl.

$R^5$ very particular preferably represents unsubstituted $C_1$-$C_6$ alkyl.

$R^5$ very particular preferably represents $C_5$ heterocyclyl substituted by one or two $C_1$-$C_4$ alkyl.

$R^5$ very particular preferably represents one of the following-groups, wherein the asterisk (*) represents the binding atom

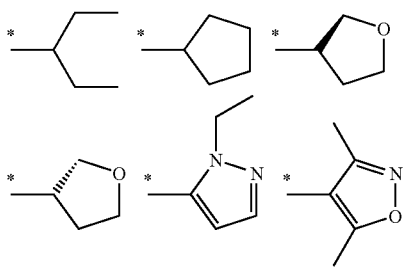

-continued

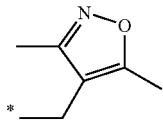

$R^6$ preferably represents hydrogen, $C_1$-$C_4$ alkyl, $C_3$-$C_7$ cycloalkyl.

$R^6$ particular preferably represents hydrogen, methyl, ethyl.

$R^7$ preferably represents hydrogen, an aryl group or a ($C_3$-$C_8$) cycloalkyl group or a ($C_1$-$C_8$)alkyl group;

wherein said aryl group, ($C_3$-$C_8$)cycloalkyl group, is unsubstituted, mono-substituted, di-substituted or tetra-substituted, the optional substituent(s) being independently selected from the group consisting of halogen, cyano, nitro, carboxy, carbamyl, hydroxy, ($C_{1-8}$)alkyl, ($C_{1-8}$)alkyl substituted by halogen, ($C_{3-8}$)cycloalkyl, ($C_{3-8}$)cycloalkyl($C_{1-8}$)alkyl, ($C_{3-8}$)cycloalkoxy, ($C_{3-8}$) cycloalkoxy($C_{1-8}$)alkyl, ($C_{3-8}$)cycloalkyl($C_{1-8}$)alkoxy, ($C_{3-8}$)cycloalkoxy($C_{1-8}$)alkoxy, aryl, aryl($C_{1-8}$)alkyl, aryloxy, aryloxy($C_{1-8}$)alkyl, aryl($C_{1-8}$)alkoxy, aryloxy ($C_{1-8}$)alkoxy, ($C_{1-8}$)alkoxy, ($C_{1-8}$)alkoxy($C_{1-8}$)alkoxy, ($C_{1-8}$)alkoxy substituted by halogen, ($C_{1-8}$)alkoxy($C_{1-8}$) alkyl, ($C_{1-8}$)alkylthio, ($C_{1-8}$)alkylthio($C_{1-8}$)alkyl, ($C_{1-8}$) alkylsulfinyl, ($C_{1-8}$)alkylsulfinyl($C_{1-8}$)alkyl, ($C_{1-8}$) alkylsulfonyl, ($C_{1-8}$)alkylsulfonyl($C_{1-8}$)alkyl, amino, ($C_{1-8}$)alkylamino, di($C_{1-8}$)alkylamino with two identical or different ($C_{1-8}$)alkyl moieties, amino($C_{1-8}$)alkyl, ($C_{1-8}$)alkylamino($C_{1-8}$)alkyl, di($C_{1-8}$)alkylamino($C_{1-8}$) alkyl with two identical or different ($C_{1-8}$)alkyl moieties in the di($C_{1-8}$)alkylamino moiety, amino($C_{1-8}$)alkoxy, ($C_{1-8}$)alkylamino($C_{1-8}$)alkoxy, di($C_{1-8}$)alkylamino ($C_{1-8}$)alkoxy with two identical or different ($C_{1-8}$)alkyl moieties, formyl, ($C_{1-8}$)alkylcarbonyl, formyloxy, ($C_{1-8}$)alkylcarbonyloxy, formyl($C_{1-8}$)alkyl, ($C_{1-8}$)alkylcarbonyl($C_{1-8}$)alkyl, formyl($C_{1-8}$)alkoxy, ($C_{1-8}$)alkylcarbonyl($C_{1-8}$)alkoxy, ($C_{1-8}$)alkoxycarbonyl, ($C_{1-8}$) alkoxycarbonyloxy, ($C_{1-8}$)alkoxycarbonyl($C_{1-8}$)alkyl, ($C_{1-8}$)alkoxycarbonyl($C_{1-8}$)alkoxy, —$OCH_2O$—, —$C(=O)OCH_2$—, —$CH_2OC(=O)$— and —$CH=CHCH=CH$—, the four last-mentioned optional substituents in each case being attached to two adjacent ring carbon atoms of the said moiety and wherein said ($C_{1-8}$)alkyl group is unsubstituted or mono-, di-, tri or tetra-substituted, the optional substituent(s) on the said ($C_{1-8}$)alkyl moiety being independently selected from the group consisting of halogen, cyano, oxo, nitro, amino, ($C_{1-8}$)alkoxy, ($C_{1-8}$)alkoxy($C_{1-8}$)alkoxy, ($C_{1-8}$) alkylthio, ($C_{1-8}$)alkylsulfinyl, ($C_{1-8}$)alkylsulfonyl, ($C_{1-8}$)alkylcarbonyloxy, ($C_{1-8}$)alkoxycarbonyl and ($C_{1-8}$)alkoxycarbonyloxy, ($C_{3-8}$)cycloalkyl, ($C_{3-8}$)cycloalkyl($C_{1-8}$)alkyl, ($C_{3-8}$)cycloalkoxy, ($C_{3-8}$)cycloalkoxy($C_{1-8}$)alkyl, ($C_{3-8}$)cycloalkyl($C_{1-8}$)alkoxy, ($C_{3-8}$)cycloalkoxy($C_{1-8}$)alkoxy, aryl, aryl($C_{1-8}$)alkyl, aryloxy, aryloxy($C_{1-8}$)alkyl, aryl($C_{1-8}$)alkoxy, aryloxy ($C_{1-8}$)alkoxy, carboxy, carbamyl, hydroxy, ($C_{1-8}$) alkoxy, ($C_{1-8}$)alkoxy($C_{1-8}$)alkoxy, ($C_{1-8}$)alkoxy substituted by halogen, ($C_{1-8}$)alkoxy($C_{1-8}$)alkyl, ($C_{1-8}$) alkylthio, ($C_{1-8}$)alkylthio($C_{1-8}$)alkyl, ($C_{1-8}$) alkylsulfinyl, ($C_{1-8}$)alkylsulfinyl($C_{1-8}$)alkyl, ($C_{1-8}$) alkylsulfonyl, ($C_{1-8}$)alkylsulfonyl($C_{1-8}$)alkyl, ($C_{1-8}$) alkylamino, di($C_{1-8}$)alkylamino with two identical or different ($C_{1-8}$)alkyl moieties, amino($C_{1-8}$)alkyl, ($C_{1-8}$) alkylamino($C_{1-8}$)alkyl, di($C_{1-8}$)alkylamino($C_{1-8}$)alkyl with two identical or different $(C_{1-8})$alkyl moieties in the di$(C_{1-8})$alkylamino moiety, amino$(C_{1-8})$alkoxy, $(C_{1-8})$alkylamino$(C_{1-8})$alkoxy, di$(C_{1-8})$alkylamino$(C_{1-8})$alkoxy with two identical or different $(C_{1-8})$alkyl moieties, formyl, $(C_{1-8})$alkylcarbonyl, formyloxy, $(C_{1-8})$alkylcarbonyloxy, formyl$(C_{1-8})$alkyl, $(C_{1-8})$alkylcarbonyl$(C_{1-8})$alkyl, formyl$(C_{1-8})$alkoxy, $(C_{1-8})$alkylcarbonyl$(C_{1-8})$alkoxy, $(C_{1-8})$alkoxycarbonyl, $(C_{1-8})$alkoxycarbonyloxy, $(C_{1-8})$alkoxycarbonyl$(C_{1-8})$alkyl, $(C_{1-8})$alkoxycarbonyl$(C_{1-8})$alkoxy.

$R^7$ particular preferably represents an aryl group or a $(C_3$-$C_8)$ cycloalkyl group or a $(C_1$-$C_8)$alkyl group, which is unsubstituted or mono-, di-, tri- or tetra-substituted on the aryl group, the optional substituent(s) on said moiety being independently selected from the group, consisting of halogen, cyano, $(C_{1-8})$alkyl, $(C_{1-8})$alkyl substituted by halogen, nitro, $(C_{1-8})$alkoxy, $(C_{1-8})$alkoxy substituted by halogen, $(C_{1-8})$alkylthio, formyloxy, $(C_{1-8})$alkylcarbonyloxy;

which is unsubstituted or mono-, di-, tri- or tetra-substituted on the $(C_3$-$C_8)$cycloalkyl group, the optional substituent(s) on said group being independently selected from the group, consisting of halogen, cyano, oxo, amino, $(C_{1-8})$alkyl, $(C_{1-8})$alkyl substituted by halogen, nitro, $(C_{1-8})$alkoxy, $(C_{1-8})$alkoxy substituted by halogen, $(C_{1-8})$alkylthio, formyloxy, $(C_{1-8})$alkylcarbonyloxy;

which is unsubstituted or mono-, di-, tri-substituted on the $(C_1$-$C_8)$alkyl group the optional substituent(s) on said moiety being independently selected from the group, consisting of halogen, cyano, hydroxy, oxo, $(C_{1-8})$alkyl, $(C_{1-8})$alkyl substituted by halogen, nitro, $(C_{1-8})$alkoxy, $(C_{1-8})$alkoxy substituted by halogen, $(C_{1-8})$alkylthio, formyloxy, $(C_{1-8})$alkylcarbonyloxy.

$R^7$ very particular preferably represents $(C_1$-$C_4)$alkyl.

n preferably represents 0 or 1.

n particular preferably represents 1.

m preferably represents 0 or 1.

m particular preferably represents 1.

In an advantageous embodiment, m represents 1 and $R^1$ is in the para position.

The invention further relates to pharmaceutically acceptable prodrugs and pharmaceutically acceptable metabolites of a compound of formula (I).

In a further preferred embodiment, compounds of the present invention are selected from the group consisting of N-(1,2-Dimethyl-propyl)4-[2-(2-methyl-5-oxo-4,4-diphenyl-4,5-dihydro-imidazol-1-yl)-acetyl]-benzamide;

N-Cyclopentyl-4-[2-(2-methyl-5-oxo-4,4-diphenyl-4,5-dihydro-imidazol-1-yl)-acetyl]-benzamide;

N,N-Diethyl-4-[2-(2-methyl-5-oxo-4,4-diphenyl-4,5-dihydro-imidazol-1-yl)-acetyl]-benzamide;

2-Ethyl-N-{4-[2-(2-methyl-5-oxo-4,4-diphenyl4,5-dihydro-imidazol-1-yl)-ethyl]-phenyl}-butyramide;

3-Methyl-N-{4-[2-2-methyl-5-oxo-4,4-diphenyl-4,5-dihydro-imidazol-1-yl)-ethyl]-phenyl}-butyramide;

1-(3,5-Dimethyl-isoxazol-4-yl)-3-{4-[2-(2-methyl-5-oxo-4-phenyl-4-propyl-4,5-dihydro-imidazol-1-yl)-acetyl]-phenyl}-urea;

1-(3,5-Dimethyl-isoxazol-4-yl)-3-(4-{2-[4-(4-fluoro-phenyl)-2-methyl-5-oxo-4-propyl-4,5-dihydro-imidazol-1-yl]-acetyl}-phenyl) urea;

2-Ethyl-N-{4-[2-(2-methyl-5-oxo-4-phenyl-4-propyl-4,5-dihydro-imidazol-1-yl)-acetyl]-phenyl}-butyramide;

2-Ethyl-N-{4-2-[4-(4-fluoro-phenyl)-2-methyl-5-oxo-4-propyl-4,5-dihydro-imidazol-1-yl]-acetyl}-phenyl)-butyramide;

1-(3,5-Dimethyl-isoxazol-4-yl)-3-{3-fluoro-4-[2-(2-methyl-5-oxo-4-phenyl-4-propyl-4,5-dihydro-imidazol-1-yl)-acetyl]-phenyl}-urea;

1-(3,5-Dimethyl-isoxazol-4-yl)-3-(3-fluoro-4-{2-[4-(4-fluoro-phenyl)-2-methyl-5-oxo-4-propyl-4,5-dihydro-imidazol-1-yl]acetyl}-phenyl)-urea;

2-Ethyl-N-{3-fluoro-4-[2-(2-methyl-5-oxo-4-phenyl-4-propyl-4,5-dihydro-imidazol-1-yl)-acetyl]-phenyl}-butyramide;

2-Ethyl-N-(3-fluoro-4-{2-[4-(4-fluoro-phenyl)-2-methyl-5-oxo-4-propyl-4,5-dihydro-imidazol-1-yl]-acetyl}-phenyl)-butyramide;

Tetrahydro-furan-3-carboxylic acid (3-fluoro-4-{2-[4-(4-fluoro-phenyl)-2-methyl-5-oxo-4-propyl-4,5-dihydro-imidazol-1-yl]-acetyl}phenyl)-amide;

Tetrahydro-furan-3-carboxylic acid {3-fluoro-4-[2-(2-methyl-5-oxo-4-phenyl-4-propyl-4,5-dihydro-imidazol-1-yl)-acetyl]-phenyl}-amide;

Tetrahydro-furan-3-carboxylic acid (4-{2-[4-(4-fluoro-phenyl)-2-methyl-5-oxo-4-propyl-4.5-dihydro-imidazol-1-yl]-acetyl}-phenyl)-amide:

2-(3,5-Dimethyl-isoxazol-4-yl)-N-(3-fluoro-4-{2-[4-(4-fluoro-phenyl)-2-methyl-5-oxo-4-propyl-4,5-dihydro-imidazol-1-yl]-acetyl}-phenyl)-acetamide;

1-(3,5-Dimethyl-isoxazol-4-yl)-3-(3-fluoro-4-{2-[4-(4-fluoro-phenyl)-2-methyl-5-oxo-4-propyl-4,5-dihydro-imidazol-1-yl]-acetyl}-phenyl)-1,3-dimethyl-urea;

2-2,4-Dimethoxy-phenyl)-N-{4-[1-hydroxy-2-(2-methyl-5-oxo-4,4-diphenyl-4,5-dihydro-imidazol-1-yl)-ethyl]-phenyl}-acetamide;

N-{4-[1-Hydroxy-2-(2-methyl-5-oxo-4,4-diphenyl-4,5-dihydro-imidazol-1-yl)-ethyl]-phenyl}-2-(2-methoxy-phenyl)-acetamide;

2-Fluoro-N-{4-[2-(2-methyl-5-oxo-4,4-diphenyl-4,5-dihydro-imidazol-1-yl)-acetyl]-phenyl}-benzamide;

N-{4-[2-2-Methyl-5-oxo-4,4-diphenyl-4,5-dihydro-imidazol-1-yl)-acetyl]-phenyl}-2-o-tolyl-acetamide;

2-Methoxy-N-{4-[2-(2-methyl-5-oxo-4,4-diphenyl-4,5-dihydro-imidazol-1-yl)-acetyl]-phenyl}-benzamide;

2-Ethyl-N-{4-[2-(2-methyl-5-oxo-4-phenyl-4-propyl-4,5-dihydro-imidazol-1-yl)-acetyl]-phenyl}-butyramide;

2-Ethyl-N-{4-[1-hydroxy-2-(2-methyl-5-oxo-4,4-diphenyl-4,5-dihydro-imidazol-1-yl)-ethyl]-phenyl}-butyramide;

1-(3,5-Dimethyl-isoxazol-4-yl)-3-{4-[2-(2-methyl-5-oxo-4,4-diphenyl-4,5-dihydro-imidazol-1-yl)-acetyl]-phenyl}-urea;

2-(2,4-Dimethoxy-phenyl)-N-{4-[2-(2-methyl-5-oxo-4,4-diphenyl-4,5-dihydro-imidazol-1-yl)-acetyl]-phenyl}-acetamide;

2-(3,5-Dimethyl-isoxazol-4-yl)-N-{4-[2-(2-methyl-5-oxo-4,4-diphenyl-4,5-dihydro-imidazol-1-yl)-acetyl]-phenyl}acetamide:

2-(2-Methoxy-phenyl)-N-{4-[2-(2-methyl-5-oxo-4,4-diphenyl-4,5-dihydro-imidazol-1-yl)-acetyl]-phenyl}-acetamide;

1-(2-Fluoro-phenyl)-3-{4-[2-(2-methyl-5-oxo-4,4-diphenyl-4,5-dihydro-imidazol-1-yl)-acetyl]-phenyl}-urea;

1-{4-[2-(2-Methyl-6-oxo-4,4-diphenyl-4,5-dihydro-imidazol-1-yl)-acetyl]-phenyl}-3-(4-nitro-phenyl)-urea;

2-Ethyl-N-{3-fluoro-4-[2-(2-methyl-5-oxo-4,4-diphenyl-4,5-dihydro-imidazol-1-yl)-acetyl]-phenyl}-butyramide;

2-Ethyl-N-{4-[2-(2-methyl-5-oxo-4,4-diphenyl-4,5-dihydro-imidazol-1-yl)-acetyl]-phenyl}-butyramide; and 2-(3,5-Dimethyl-isoxazol-4-yl)-N-(3-fluoro-4-{2-[4-(4-fluoro-phenyl)-2-methyl-5-oxo-4-propyl-4,5-dihydro-imidazol-1-yl]-acetyl}-phenyl)-acetamide;

and pharmaceutically acceptable salts thereof.

In a further aspect, the invention relates to processes for the preparation of compounds of the formula I and their salts. Compounds of formula (I) are obtainable according to the processes which are summarized by the following scheme.

carbonate or triethylamine, optionally in the presence of a solvent, e.g. acetone, DMF, followed, when starting from formulas (III) and (IV), by hydrolysis (e.g. treatment with aqueous HCl); and when starting from formula (V) by a reduction reaction (e.g. treatment with SnCl2).

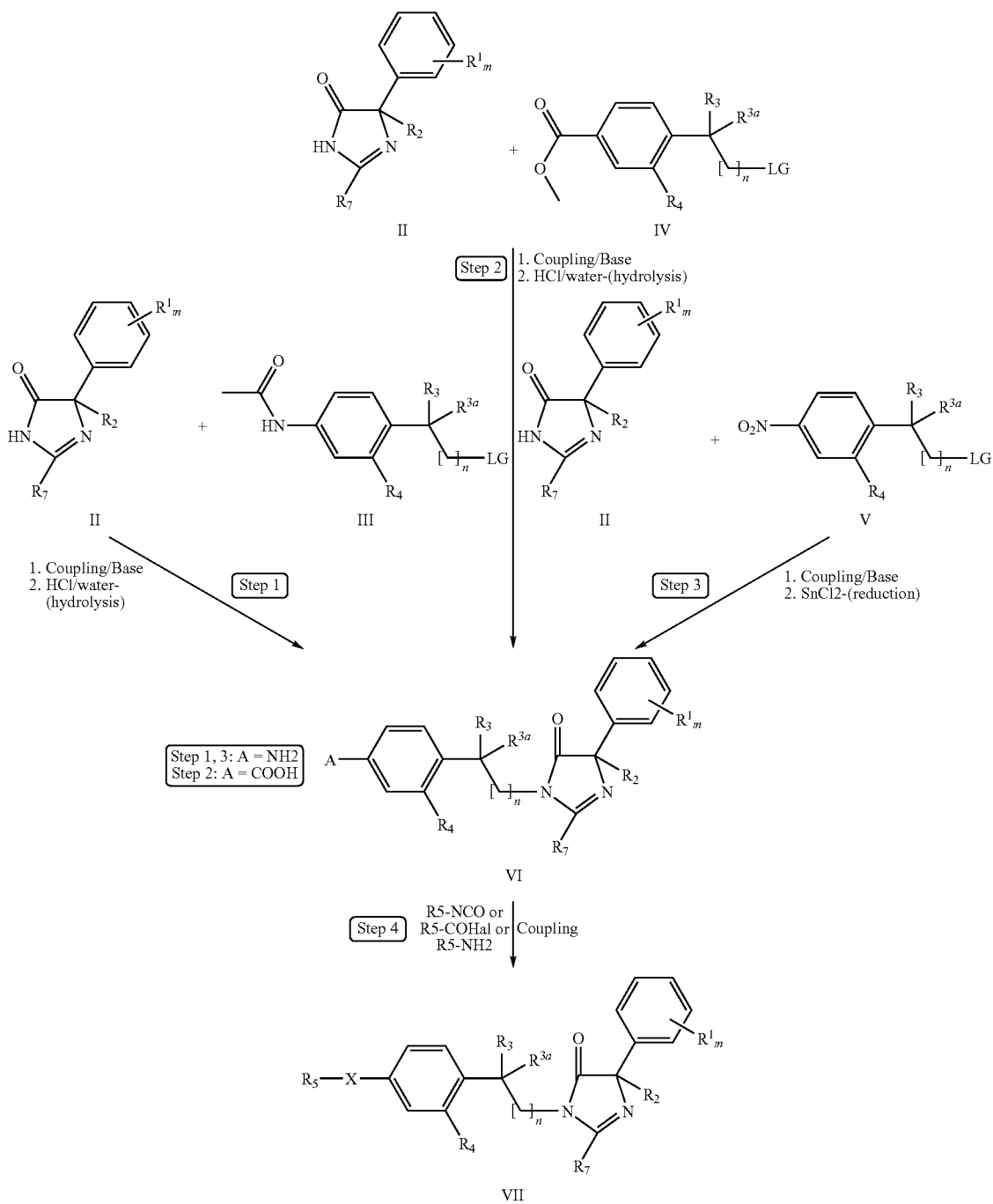

The processes are described in more detail below.

Steps 1,2,3: A compound of formula (VI) is obtainable by reacting a compound of formula (II) wherein the substituents are as defined for formula (I) with a compound of formula (III) or (IV) or (V) where LG is a leaving group such as bromo or chloro in the presence of a suitable base e.g. potassium Step 4: A compound of formula (I) is obtainable by reacting a compound of formula (VI) with amide or urea forming reagents like acids, isocyanates or in case of inverse amides reacting with amines Thus, the invention relates to a process for manufacturing a compound of formula I comprising the steps of A (to obtain a compound of formula (I) wherein X represents —N(H)—C(O)—N(H)—): reacting of a compound of the formula (VI)

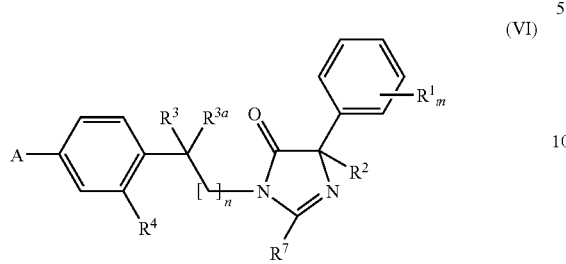

(VI)

wherein A represents an amino group and the remaining substituents are as defined for the formula (I), with a compound of the formula (VII-A)

R⁵—NCO    (VII-A)

wherein R⁵ is as defined in formula (I)

or

B (to obtain a compound of formula (I) wherein X represents —C(O)—N(H)—): reacting a compound of formula (VI)

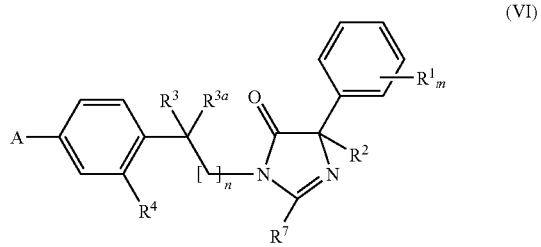

(VI)

wherein A represents an amino group and the remaining substituents are as defined for the formula (I), with a compound of the formula (VII-B)

R⁵C(O)-LG    (VII-B)

wherein R⁵ is as defined in formula (I) and LG represents a leaving group, such as a halogen, or C (to obtain a compound of formula (I) wherein X represents —N(H)—C(O)—): reacting a compound of formula (VI)

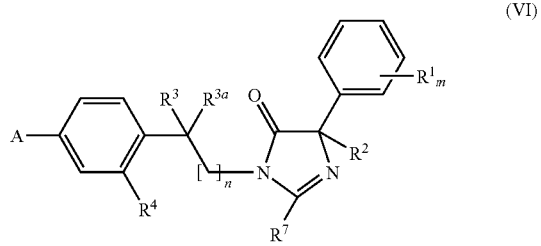

(VI)

wherein A represents a carboxy group and the remaining substituents are as defined for the formula (I), with a compound of the formula (VII-B)

R⁵—NH₂    (VII-C)

wherein R⁵ is as defined in formula (I);

in each case: optionally in the presence of a base, such as a hydride; optionally in the presence of one or more diluents; optionally followed by reduction, oxidation or functionalization reaction of the resulting compound of formula (I); optionally followed by cleavage of protecting groups if present; optionally followed by recovering the so obtainable compound of the formula (I) in free base form or in acid addition salt form.

The reactions can be effected according to conventional methods, for example as described in the Examples. The working-up of the reaction mixtures and the purification of the compounds thus obtainable may be carried out in accordance with known procedures. Acid addition salts may be produced from the free bases in known manner, and vice-versa.

Compounds of the formula I can also be prepared by further conventional processes, e.g. as described in the Examples, which processes are further aspects of the invention.

The starting materials of the formulae II-VI are known or may be prepared according to conventional procedures starting from known compounds, for example as described in the Examples. Selected starting materials and intermediates of the formulae II-VI are unknown and subject of the present invention.

It was further found that compounds of the formula I and their pharmaceutically acceptable acid addition salts, hereinafter also referred to as "agents of the invention", exhibit valuable pharmacological properties, when tested in vitro and in animals, and are, therefore, useful as active ingredients in medicaments.

Thus, the invention relates in a further aspect to a compound of formula (I) as medicament.

It was further found that compounds of the formula I and their pharmaceutically acceptable acid addition salts, hereinafter also referred to as "agents of the invention", exhibit valuable pharmacological properties in the treatment of NPY Y2 related conditions, diseases or disorders and are, therefore, useful as active ingredients in medicaments for the treatment of such conditions, disorders or diseases.

It was surprisingly found that agents of the invention have good efficacy as selective ligands for NPY Y2 receptors, showing desirable NPY Y2 receptor modulating activities at various receptor subtypes, and, moreover, may possess interesting pharmacokinetic properties, e.g. improved oral bioavailability or enhanced metabolic stability.

Thus, in a further aspect, the invention provides a method for the treatment, prevention or delay of progression of a condition, disease or disorder, that can be modulated or is mediated by NPY Y2 receptor comprising administering to a subject in need thereof a therapeutically effective amount of a compound of the formula I in free form or in pharmaceutically acceptable salt form.

The invention also provides the use of a compound of the formula (I) in free form or in pharmaceutically acceptable salt form, for the manufacture of a medicament for the treatment, prevention or delay of progression of a condition, disease or disorder, that can be modulated or is mediated by NPY Y2 receptors.

The invention therefore relates to novel non-peptidic NPY Y2 receptor modulators, in particular inhibitors, useful in treating or preventing disorder: anxiety disorders and depression; injured mammalian nerve tissue; a condition responsive to treatment through administration of a neurotrophic factor; a neurological disorder; bone loss; substance related disorders; sleep/wake disorders; cardiovascular disease; metabolic disorders such as obesity; or an obesity-related disorder.

Compounds of the invention are also useful in modulating endocrine functions; particularly endocrine functions controlled by the pituitary and hypothalamic glands, and maybe used to treat inovulation and infertility.

Neuropeptide Y (NPY) is a highly conserved 36 amino acid peptide that belongs to the pancreatic polypeptide (PP) family and was first isolated from mammalian brain in 1982 (Tatemoto et al., 1982, Nature, 296, 659). NPY sequences from a number of animal species have been elucidated and all show a high degree of amino acid homology to the human protein (see Larhammar, D. in "The Biology of Neuropeptide Y and Related Peptides", Colmers, W. F. and Wahlestedt, C. Eds., Humana Press, Tôtowa, N.J. 1993). NPY is one of the most abundant neuropeptides in the mammalian central (CNS) and peripheral nervous systems (PNS) and controls a wide spectrum of basic physiological functions. NPY strongly stimulates food intake, affects blood pressure and cardiovascular function through its vasoconstricting properties, induces anxiolysis, affects circadian rhythms and controls certain aspects of endocrine hypothalamic and pituitary functions (Heilig and Widerlöv, 1995; Thorsell and Heilig, 2002). Furthermore, evidence has accumulated supporting a role of NPY in memory processing, drug and alcohol abuse, pain, and epilepsy (Silva et al., 2002). Among the potential physiological properties of NPY, its orexigenic effect has been most widely studied and was first suggested by the demonstration that NPY potently stimulates food intake following acute injection into the brain ventricles or into specific hypothalamic sites such as the paraventricular nucleus in rats (Levens and Della-Zuana, 2003).

In mammals, the NPY gene is expressed in neurons where NPY itself is mainly found. In the brain, NPY is expressed at high levels in hypothalamic areas, nucleus accumbens, septum, and periaqueductal gray matter. Moderate expression levels of NPY are found in amygdala, hippocampus, thalamus, and basal ganglia. NPY expression is almost absent in the pons and cerebellum. In the forebrain, the interneurons are the predominant NPY-immunoreactive neurons (Thorsell and Heilig, 2002).

At the cellular level, NPY exerts its biological effects through an interaction with a portfolio of receptors. Presently, five receptors for NPY have been characterized based upon binding profile, pharmacological characterization, and cDNA sequence—Y1, Y2, Y2, Y2, and Y6 (Kaga, T. et al. Peptides 2001, 22, 501-506; Wahlestedt, C. et al. Ann. N.Y. Acad. Sd. 1990, 611, 7; Larhammar, D. et al. J. BioJ. Chem. 1992, 267, 10935; Wahlestedt, C. et al. Regul Pept. 1986, 13, 307; Fuhlendorff, J. U. et al. Proc. Natl. Acad. Sd. U.S.A. 1990, 87, 182; Grundemar, L. et al. J. Pharmacol. Exp. Ther. 1991, 258, 633; Laburthe, M. et al. Endocrinology 1986, 118, 1910; Castan, I. et al. Endocrinology 1992, 131, 1970: Gerald, C. et al. Nature 1996, 382, 168; Weinberg, D. H. et al. J. Biol. Chem. 1996, 271, 16435; Gehlert, D. et al. Curr. Pharm. Des. 1995, 1, 295; Lundberg, J. M. et al. Trends Pharmacol. Sci. 1996, 17, 301). The NPY $Y_6$ receptor is not functional in humans while NPY does not bind to human $Y_4$ receptors. A Y3 has not been cloned but only pharmacologically characterized (Michel et al., 1998; Silva et al., 2002). All NPY receptors belong to the family of the so-called G-protein coupled receptors (GPCRs). Among the typical signaling responses of NPY receptors are inhibition of adenylyl cyclase and increase of intracellular calcium concentration through IP3-dependent mobilization of intracellular calcium stores or via action on calcium channels.

Binding of NPY to its receptors can elicit a variety of pharmacological and biological effects in vitro and in vivo. A host of preclinical evidence has accumulated supporting a role of NPY in the control of anxiety-like behavior. For example, when administered to the brain of live animals (intracerebroventricularly (icv) or into the amygdala), NPY produced anxiolytic-like effects in established animal models of anxiety such as the elevated plus-maze, Vogel punished drinking, and Geller-Seifter's bar-pressing conflict paradigms, and fear-potentiated startle (Broqua et al., 1995; Thorsell and Heilig, 2002; Heilig, M. et al. Psychopharmacology 1989, 98, 524: Heilig, M. et al. Regul. Pept. 1992, 41, 61; Heilig, M. et al. Neuropsychopharmacology 1993, 8, 357). In humans intravenous administration of NPY has been shown to inhibit hypothalamic-pituitary-adrenal (HPA) axis activity, promote sleep and modulate REM sleep (Antonijevic et al., 2000). Thus, compounds that mimic NPY are postulated to be useful for the treatment of anxiety disorders and sleep disorders.

NPY immunoreactivity is significantly decreased in the cerebrospinal fluid (CSF) of patients with major depression and those of suicide victims (Widdowson, P. S. et al. J. Neurochem. 1992, 59, 73), and rats treated with tricyclic antidepressants displayed significant increases of NPY levels relative to vehicle-treated animals (Heilig, M. et al). Eur. J. Pharmaco). 1988, 147, 465). These findings suggest that an inadequate NPY response may play a role in the pathophysiology of depression, and that compounds that regulate and potentiate the NPY-ergic system may be useful for the treatment of depression.

It is well accepted that the anxiolytic properties of NPY are mediated through its postsynaptic Y1 receptors, whereas presynaptic Y2 receptors negatively modulate the release of NPY and that of other neurotransmitters (such as GABA, glutamate and others). Consequently, Y2 receptor blockade may lead to enhanced GABA-ergic and NPY-ergic effects and thus Y2 receptor antagonists may prove useful in the treatment of depression and anxiety.

NPY improved memory and performance scores in animal models of learning (Flood, J. F. et al. Brain Res. 1987, 421, 280) and therefore may serve as a cognition enhancer for the treatment of neurodegenerative diseases such as Alzheimer's Disease (AD) as well as AIDS-related and senile dementia.

Elevated plasma levels of NPY were present in animals and humans experiencing episodes of high sympathetic nerve activity such as surgery, newborn delivery, and hemorrhage (Morris, M. J. et. al. J. Auton. Nerv. Syst 1986, 17, 143). Thus, chemical substances that alter the NPY-ergic system may be useful for alleviating migraine, pain, and the condition of stress. NPY also mediates endocrine functions such as the release of luteinizing hormone (LH) in rodents (Kalra, S. P. et. al. Front. Neuroendrocrinol. 1992, 13, 1). Since LH is vital for mammalian ovulation, a compound that mimics the action of NPY could be useful for the treatment of infertility, particularly in women with so-called luteal phase defects.

Release of NPY and activation of NPY Y2 receptors stimulates fat angiogenesis and the proliferation and angiogenesis of new adipocytes, resulting in abdominal obesity and a metabolic syndrome-like condition in mice. While NPY was shown to stimulate mouse and human fat growth, local abdominal fat-delivered NPY Y2 receptor antagonist decreased adipose tissue weight and volume in both obese and lean mice by 50%. The lipolytic effect of Y2 receptor blockade was accompanied by decreased vascularity and increased apoptosis in the abdominal fat pads (Kuo, L. E. et al. Nat. Med. 2007 13(7), 803). Thus, compounds that block NPY Y2 receptors may be useful for the treatment of obesity and metabolic disorders. Furthermore, local administration of NPY Y2 receptor antagonists might be useful for nonsurgical localized removal of fat (pharmacological lipolysis).

Y2 receptor knockout mice displayed reduced body weight despite an increase in food intake, possibly due to the lack of the feedback inhibition of the postprandially released anorectic peptide PYY3-36 (Batterham, R. L. et al. Nature 2002, 418, 650-654). The Y2 receptor knockout mice also showed a significant increase in bone mineral density (Baldock, P. A. J. Clin. Invest. 2002, 109, 915-921). Furthermore, hypothalamic specific deletion of Y2 receptors in adult Y2 receptor floxed mice was reported to produce an increase in bone mineral density. Thus NPY Y2 antagonists may be useful for the prevention and treatment of osteoporosis.

A direct link between NPY signaling and regulation of ethanol consumption was suggested by the demonstration that NPY overexpression in mice reduced ethanol self-administration, whereas NPY knockout increased ethanol self-administration (Thiele et al. Nature 1998, 396, 366-369). Studies have also indicates that the Y2 receptor is involved in the neurobiological responses to ethanol and other drugs of abuse. Thiele and coworkers (Neuropeptides, 2004, 38(4), 235-243; Peptides 2004, 25(6), 975-983) described low ethanol consumption of Y2 receptor knockout mice, as well as their increased voluntary water consumption. Recently, it has been demonstrated that icv administration of BIIE0246, a selective NPY Y2 antagonist, dose dependently reduced ethanol self-administration in rats (Thorsell et al. Neurosci. Lett. 2002, 332, 1-4). Therefore, NPY Y2 receptor antagonists may be useful for the treatment of alcohol and drug abuse.

Additionally, NPY Y2 antagonists have been suggested for the prevention of cardiovascular disease, for example, sudden death due to cardiac arrhythmias, post-myocardial infarction, or heart failure (See: Intl. Pat. Appl. Publ. WO 02/1083137, Oct. 24, 2002).

The invention includes also pharmaceutically acceptable salts of the compounds represented by Formula I. Pharmaceutically acceptable salts of the above-described specific compounds are especially preferred. See, e.g., S. M. Berge, et al., "Pharmaceutical Salts", J. Pharm. Sd., 1977, 66:1-19, and Handbook of Pharmaceutical Salts, Propertions, Selection, and Use; Stahl, R H., Wermuth, C. G., Eds.; Wiley-VCH and VHCA: Zurich, 2002.

However, salts of acids and bases that are non-pharmaceutically acceptable may also find use, for example, in the preparation or purification of a pharmaceutically acceptable compound. All salts, whether pharmaceutically acceptable or not are included within the ambit of the present invention. A "pharmaceutically acceptable salt" is intended to mean a salt of a free acid or base of a compound represented by Formula I that is not toxic, biologically intolerable, or otherwise biologically undesirable. Preferred pharmaceutically acceptable salts are those that are pharmacologically effective and suitable for contact with the tissues of patients without undue toxicity, irritation, or allergic response.

The invention also relates to treatment methods employing pharmaceutically acceptable prodrugs of the compounds of Formula I. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I) or (H)) A "pharmaceutically acceptable prodrug" is a prodrug that is not toxic, biologically intolerable, or otherwise biologically unsuitable for administration to the subject. Conventional procedures for the selection and preparation of suitable prodrug derivatives are described, for example, in "Design of Prodrugs", ed. H. Bundgaard, Elsevier, 1985. Exemplary prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula I.

Pharmaceutically active metabolites may also be used in the methods of the invention. A "pharmaceutically active metabolite" means a pharmacologically active product of metabolism in the body of a compound of Formula I or salt thereof. Prodrugs and active metabolites of a compound may be determined using routine techniques known or available in the art. See, e.g., Bertolini et al., J. Med. Chem. 1997, 40, 2011-2016; Shan et al., J. Pharm. Sd. 1997, 86(7), 765-767: Bagshawe, Drug Dev. Rs. 1995, 34, 220-230; Bodor, Adv. Drug Res. 1984, 13, 224-331; Bundgaard, Design of Prodrugs (Elsevier Press, 1985); and Larsen, Design and Application of Prodrugs, Drug Design and Development (Krogsgaard-Larsen et al., eds., Harwood Academic Publishers, 1991).

The compounds of Formula I and their pharmaceutically acceptable salts, pharmaceutically acceptable prodrugs, and pharmaceutically active metabolites of the present invention are useful as NPY Y2 modulators, in particular inhibitors, in the methods of the invention. The agents may be used in the inventive methods for the treatment or prevention of medical conditions, diseases, or disorders mediated through inhibition or modulation of NPY Y2, such as those described herein. Compounds of the invention are potent, non-peptidic, low molecular weight, selective NPY Y2 inhibitors and are useful in treating or preventing: anxiolytic disorders and depression; injured mammalian nerve tissue; conditions responsive to treatment through administration of a neurotrophic factor; neurological disorders; bone loss; substance related disorders; sleepawake disorders; cardiovascular disease; and metabolic disorders such as obesity or an obesity-related disorder. Compounds of the invention modulate endocrine functions, particularly those controlled by the pituitary and hypothalamic glands, and therefore may be used to treat inovulation and infertility that may be due to insufficient release of luteinizing hormone (LH) or luteal phase defect. Compounds of the invention are also useful in the treatment of chronic heart failure, The compounds compete with the endogenous ligands NPY and related peptides and possibly non-endogenous ligands, and bind to the NPY Y2 receptor. In addition, the compounds demonstrate antagonist activity by antagonizing the action of NPY upon binding to the Y2 receptor. Symptoms or disease states are intended to be included within the scope of "medical conditions, disorders, or diseases." For example, "anxiety disorders" include affective disorders such as anxiety, generalized anxiety disorder (GAD), panic disorder, phobias, obsessive-compulsive disorder (OCD), stress disorders including post-traumatic stress disorder (PTSD), hemorrhagic stress, stress-induced psychotic episodes, psychosocial dwarfism, stress headaches, stress-induced immune systems disorders such as stress-induced fever, and stress-related sleep disorders, and can include eating disorders such as anorexia nervosa, bulimia nervosa, obesity, and drug addiction.

"Depression" refers to major depressive disorders, cyclothymia, dysthymia, bipolar or manic disorders, and the like.

"Nerve tissue" as used herein refers to any vertebrate nerve tissue, particularly including mammalian cells of the central nervous system (CNS) and peripheral nervous system (PNS). More particularly, nerve tissue includes spinal cord neuronal structures, peripheral nervous system nerves, and even nerve cells of the brain.

"Nerve tissue injury", "injured mammalian nerve tissue", or "CNS or PNS nerve tissue injury" include any damage to relevant nerve tissue irrespective of cause, e.g., injuries attributable to trauma including but not limited to nerve tissue lesions, traumatically-induced compression, tumors, hemorrhage, infectious processes, spinal stenosis, or impaired blood supply.

"Treating injured mammalian nerve tissue" includes, but is not limited, to the in vivo administration of compounds, compositions, and methods of the instant invention to restore action potential or nerve impulse conduction through a nerve tissue lesion. The term may also include such administration in an effort to reduce the damaging effects of any injury to mammalian nerve tissue, whether through restoration of action potential or nerve impulse conduction, by simulating growth or proliferation of nervous tissue, by ameliorating unwanted conditions in the extracellular microenvironment near an injury, or otherwise.

"Neurotrophic factor", as used herein, refers to compounds that are capable of stimulating growth or proliferation of nervous tissue, including compounds of the instant invention and known neurotrophic factors described previously herein.

"Neurological disorders" include CNS disorders such as tinitus, spasticity, and neuropathic pain, supranuclear palsy, AIDS related dementias, multiinfarct dementia, neurodegenerative disorders such as Alzheimer's disease, Parkinson's disease, and Huntington's disease, head trauma, spinal cord trauma, ischemic neuronal damage, amyotrophic lateral sclerosis, and disorders of pain perception such as fibromyalgia and epilepsy.

"Bone loss" refers to enhancement of bone growth or prevention of bone loss caused by conditions such as osteoporosis, osteomalacia, Paget's disease, disorders of bone homeostasis, and the like.

"Substance related disorders" refer to misuse, addiction, or dependence disorders related to the consumption of alcohol, amphetamines (such as, for example, 3,4-methylene-dioxy-N-methylamphetamine, also known as "MDMA" or "ecstacy"), cannabis, hallucinogens (such as, for example, cocaine), inhalants, nicotine, opioids, phencydildine, narcotics, or sedatives, or combinations thereof.

"Sleep/wake disorders" include narcolepsy; sleep apnea disorders such as central sleep apnea, obstructive sleep apnea, and mixed sleep apnea; hypersomnia, including excessive daytime sleepiness (EDS), and, in particular, hypersomnia associated with narcolepsy or sleep apnea disorder, sleep/wake disturbances associated with attention deficit hyperactive disorder (ADHD); circadian rhythm abnormalities such as delayed sleep phase syndrome, advance sleep phase syndrome, non-24 hour sleep/wake disorder, jet lag, or shift-work disorder; parasomnia disorders such as somnambulism, pavor nocturnus, REM sleep behavior disorder, sleep bruxism, or sleep enuresis; sleep-related movement disorders such as sleep bruxism, restless legs syndrome, or periodic limb movement; insomnia, including extrinsic insomnia, psychophysiologic insomnia, drug-dependent insomnia, or alcohol-dependent insomnia; sleep/wake disturbances associated with mental disorders such as depression, anxiety, schizophrenia, or other psychotic disorders; sleep/wake disturbances associated with neurological disorders such as migraine, epilepsy, Parkinson's disease, or Alzheimer's disease; and sleep/wake disturbances associated with fibromyalgia, headaches, gastroesophageal reflux disease, coronary artery ischemia, cardiac arrhythmias, abnormal swallowing, choking, or laryngospasm.

"Obesity" refers to a condition in which a subject has a body mass index of greater than or equal to 30. "Over-weight" refers to a condition in which a subject has a body mass index of greater or equal to 25.0. The body mass index and other definitions are according to the "NIH Clinical Guidelines on the Identification and Evaluation, and Treatment of Over-weight and Obesity in Adults" (1998).

"Obesity-related disorder" includes anorexia nervosa, wasting, AIDS-related weight loss, bulimia, cachexia, lipid disorders including hyperlipidemia and hyperuricemia, insulin resistance, noninsulin dependent diabetes mellitus (NIDDM, or Type II diabetes), insulin dependent diabetes mellitus (IDDM or Type I diabetes), diabetes-related complications including microangiopathic lesions, ocular lesions, retinopathy, neuropathy, and renal lesions, cardiovascular disease including cardiac insufficiency, coronary insufficiency, and high blood pressure, atherosclerosis, atheromatous disease, stroke, hypertension, Syndrome X, gallbladder disease, osteoarthritis, sleep apnea, forms of cancer such as uterine, breast, colorectal, kidney, and gallbladder, high cholesterol levels, complications of pregnancy, menstrual irregularities, hirsutism, muscular dystrophy, infertility, and increased surgical risk.

"Cardiovascular disease" includes, for example, cardiac arrhythmia, post-myocardial infarction, and heart failure.

Thus, the pharmaceutical agents may be used to treat subjects diagnosed with or suffering from a disease, disorder, or condition mediated through NPY Y2 activity.

The term "treat" or "treating" as used herein is intended to refer to administration of at least one agent of the invention or a composition of the invention to a subject for the purpose of effecting a therapeutic or prophylactic benefit through modulation of NPY Y2 activity. Treating includes reversing, ameliorating, alleviating, inhibiting the progress of, lessening the severity of, or preventing a disease, disorder or condition, or one or more symptoms of such disease, disorder or condition mediated through modulation of NPY Y2 activity.

The term "subject" refers to a mammalian patient in need of such treatment, such as a human. "Modulators" include both inhibitors and activators, where "inhibitors" refer to compounds that decrease, prevent, inactivate, desensitize or down-regulate NPY Y2 expression, activity or function, and "activators" are compounds that increase, activate, facilitate, sensitize, or up-regulate NPY Y2 expression, activity, or function.

Accordingly, the invention relates to methods of using the pharmaceutical agents described herein to treat subjects diagnosed with or suffering from a disease, disorder, or condition mediated through NPY Y2 activity, such as: anxiety disorders and depression; injured mammalian nerve tissue; conditions responsive to treatment through administration of a neurotrophic factor; neurological disorders; bone loss; substance related disorders; metabolic disorders such as obesity or an obesity-related disorder, inovulation and infertility that may be due to insufficient release of luteinizing hormone (LH) or luteal phase defect; and cardiovascular disease, cardiac arrhythmia, post-myocardial infarction, or chronic heart failure. In particular, the invention relates to methods of using the pharmaceutical agents described herein to treat subjects diagnosed with or suffering from a disease, disorder, or condition mediated through NPY Y2 activity, such as anxiety and alcoholism.

In certain preferred embodiments of the method, the disease, disorder, or medical condition is selected from: anxiety disorders and depression; a condition requiring treatment of injured mammalian nerve tissue; a condition amenable to treatment through administration of a neurotrophic factor; a neurological disorder; bone loss; substance related disorders; sleep/wake disorders; cardiovascular disease such as cardiac arrhythmia, post-myocardial infarction, or heart failure; obesity; an obesity-related disorder; and a condition related to an endocrine function including inovulation and infertility.

Furthermore, the agents of the invention may be useful in the prevention, treatment or delay of progression of disorders of the gastro-intestinal tract mediated full or in part by NPY Y2 receptors.

Disorders of the gastrointestinal tract include Gastro-Esophageal Reflux Disease (GERD), idiopathic and diabetic gastroparesis, post-operative ileus, and Functional Gastrointestinal Disorders (FGIDs).

GERD is defined as chronic symptoms or mucosal damage produced by the abnormal reflux in the esophagus. This is commonly due to transient or permanent changes in the barrier between the esophagus and the stomach. Gastroparesis, also called delayed gastric emptying, is a medical condition consisting of a paresis (partial paralysis) of the stomach ("gastro-"), resulting in food remaining in the stomach for a longer period of time than normal, and is often associated with feelings of discomfort. Post-operative Ileus is defined as failure of aboral passage of intestinal contents due to transient impairment of GI motility following abdominal surgery. FGIDs are defined as chronic or recurrent conditions associated with abdominal symptoms without organic cause using conventional diagnostic measures. A cardinal symptom present in many FGIDs is visceral pain and/or discomfort. FGIDs include functional dyspepsia (FD), functional heartburn (a subset of GERD), irritable bowel syndrome (IBS) associated with constipation and/or diarrhea, functional bloating, functional diarrhea, chronic constipation, functional disturbancies of the biliary tract as well as other conditions according to Gut 1999, Vol. 45 Suppl. II.

The agents of the present invention may be useful for the prevention of the above-mentioned conditions and disorders.

The agents of the present invention may be useful for the treatment of the above-mentioned conditions and disorders.

The agents of the present invention may be useful for the delay of progression of the above-mentioned conditions and disorders.

The usefulness of the agents of the invention in the treatment of the above-mentioned disorders can be confirmed in a range of standard tests including those indicated below:

Activity of the agents of the invention in GERD can be demonstrated in standard models that measure gastric distension-induced transient lower esophageal sphincter relaxations (TLESRs) in dogs according to Stakeberg, J. and Lehmann, A. Neurogastroenterol. Mot. (1999) 11: 125-132. At doses of about 0.03 to about 10 mg/kg i.p., s.c. or p.o., selected agents of the invention may reduce the occurrence of TLESRs.

Activity of the agents of the invention in gastroparesis can be demonstrated in standard models that measure gastric emptying such as the breath test (methodology according to Schoonjans R. et al., Neurogastroenterol. Mot. (2002) 14: 287-293) or near infrared fluorescent imaging (methodology according to Gremlich et al., J. Mol. Imaging (2004) 3: 303-311). At doses of about 0.03 to about 10 mg/kg i.p., s.c. or p.o., selected agents of the invention may increase gastric emptying in either mice, rats or dogs.

Activity of the agents of the invention in functional dyspepsia can be demonstrated by a model that assesses fasted gastric tone and gastric accommodation to a meal in rats by measuring the intragastric pressure during meal infusion (methodology according to Janssen P. et al., Scand J. Gastroenterology (2007) 43: 34-43). At doses of about 0.03 to about 10 mg/kg i.p., s.c. or p.o., selected agents of the invention may decrease gastric pressure during meal infusion.

Furthermore, the activity of the agents of the invention in functional dyspepsia can be demonstrated in a model of fasted gastric tone and gastric accommodation to meal in dogs (methodology according to Lei et al., Dig. Dis. Sci. (2005) 50:2134-40). At doses of about 0.03 to about 10 mg/kg p.o., selected agents of the invention may increase the gastric volume in fasting conditions indicative of a reduced gastric tone.

Activity of the agents of the invention in post-operative ileus can be demonstrated in standard models to measure gastrointestinal motility after abdominal surgery (according to Huge, A. et al., J. Surg. Res (1998) 74: 112-118). At doses of about 0.03 to about 10 mg/kg i.p., s.c. or p.o., selected agents of the invention may induce a faster restauration of gastrointestinal motility as compared to vehicle/placebo treatment.

For the above-mentioned indications, the appropriate dosage will vary depending on, e.g., the compound employed, the host, the mode of administration and the nature and severity of the condition, disorder or disease. However, in general, satisfactory results in animals are indicated to be obtained at a daily dosage of from about 0.1 to about 100, preferably from about 1 to about 50, mg/kg of animal body weight. In larger mammals, for example humans, an indicated daily dosage is in the range of from about 10 to about 2000, preferably from about 10 to about 200, mg of an agent of the invention conveniently administered, for example, in divided doses up to four times a day or in sustained release form.

An agent of the invention may be administered by any conventional route, in particular enterally, preferably orally, for example in the form of tablets or capsules, or parenterally, for example in the form of injectable solutions or suspensions.

In accordance with the foregoing, in a further aspect, the invention relates to an agent of the invention, for use as a medicament, e.g. for the treatment or prevention of conditions, disorders or diseases, that can be modulated or are mediated by NPY Y2 receptors.

In a further aspect, the invention relates to the use of an agent of the invention as active ingredient in a medicament, e.g. for the treatment or prevention of conditions, disorders or diseases, that can be modulated or are mediated by NPY Y2 receptors.

In a further aspect, the invention relates to a pharmaceutical composition comprising an agent of the invention as active ingredient in association with at least one pharmaceutical carrier or diluent. Such compositions may be manufactured in conventional manner. Unit dosage forms contain, for example, from about 1 to about 1000, preferably from about 1 to about 500, mg of an agent of the invention.

In a further aspect, the invention relates to the use of an agent of the invention for the manufacture of a medicament for the treatment or prevention of conditions, disorders or diseases, that can be modulated or are mediated by NPY Y2 receptors.

In a further aspect, the invention relates to a method for the treatment or prevention of conditions, disorders or diseases, that can be modulated or are mediated by NPY Y2 receptors, in a subject in need of such treatment, which comprises administering to such subject a therapeutically effective amount of an agent of the invention.

In a further aspect, the invention relates to pharmaceutical compositions each comprising: (a) an effective amount of an agent selected from compounds of Formula I and pharmaceutically acceptable salts, pharmaceutically acceptable prodrugs, and pharmaceutically active metabolites thereof; and (b) a pharmaceutically acceptable excipient.

In a treatment method according to the invention, an effective amount of at least one pharmaceutical agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment. Effective amounts or doses of the agents of the present invention may be ascertained by routine methods such as modeling, dose escalation studies, or clinical trials, and by taking into consideration routine factors, e.g., the mode or route of administration or drug delivery, the pharmacokinetics of the agent, the severity and course of the disease, disorder, or condition, the subjects previous or ongoing therapy, the subject's health status and response to drugs, and the judgment of the treating physician. An exemplary dose is in the range of from about 0.001 to about 200 mg of agent per kg of subject's body weight per day, preferably about 0.05 to 100 mg/kg/day, or about to 35 mg/kg/day, in single or divided dosage units (e.g., BID, TID, OID). For a 70-kg human, an illustrative range for a suitable dosage amount is from about 0.05 to about 7 g/day, or about 0.2 to about 2.5 g/day.

Once improvement of the patient's disease, disorder, or condition has occurred, the dose may be adjusted for preventative or maintenance treatment.

For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

The agents of the invention can be administered alone or as combination with other pharmaceutical agents effective, e.g., in the treatment or prevention of conditions, disorders or diseases mentioned above. Such pharmaceutical combinations may be in the form of a unit dosage form, whereby each unit dosage will comprise a predetermined amount of the two components in admixture with at least one pharmaceutical carrier or diluent. Alternatively, the combination may be in the form of a package containing the two components separately, e.g. a pack or dispenser-device adapted for the concomitant or separate administration of the two active agents, wherein these agents are separately arranged. In a further aspect, the invention relates to such pharmaceutical combinations.

The additional compounds may be co-administered separately with an agent of Formula I or included with such an agent as an additional active ingredient in a pharmaceutical composition according to the invention. In an exemplary embodiment, additional active compounds are those that are known or discovered to be effective in the treatment of conditions, disorders, or diseases mediated by NPY Y2 activity, such as another NPY Y2 modulator or a compound active against another target associated with the particular condition, disorder, or disease. The combination may serve to increase efficacy (e.g., by including in the combination a compound potentiating the potency or effectiveness of an agent according to the invention), decrease one or more side effects, or decrease the required dose of the agent according to the invention. In one illustrative embodiment, a composition according to the invention may contain one or more additional active ingredients selected from anxiolytics, antidepressants, and hypnotics. The agents of the invention are used, alone or in combination with one or more other active ingredients, to formulate pharmaceutical compositions of the invention. A pharmaceutical composition of the invention comprises: (a) an effective amount of at least one pharmaceutical agent in accordance with the invention; and (b) a pharmaceutically acceptable excipient.

A "pharmaceutically acceptable excipient" refers to a substance that is not toxic, biologically intolerable, or otherwise biologically unsuitable for administration to a subject, such as an inert substance, added to a pharmacological composition or otherwise used as a vehicle, carrier, or diluent, to facilitate administration of a pharmaceutical agent and that is compatible therewith Examples of excipients include calcium carbonate, calcium phosphate, various sugars and types of starch, cellulose derivatives, gelatin, vegetable oils, and polyethylene glycols, Delivery forms of the pharmaceutical compositions containing one or more dosage units of the pharmaceutical agents may be prepared using suitable pharmaceutical excipients and compounding techniques now or later known or available to those skilled in the art. The compositions may be administered in the inventive methods by oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the compounds of the invention can be provided in the form of tablets or capsules, or as a solution, emulsion, or suspension.

To prepare the oral compositions, the agents may be formulated to yield a dosage of, e.g., from about 0.05 to about 50 mg/kg daily, or from about 0.05 to about 20 mg/kg daily, or from about 0.1 to about 10 mg/kg daily.

Oral tablets may include the active ingredient mixed with pharmaceutically acceptable excipients such as inert diluents, disintegrating agents, binding agents, lubricating agents, sweetening agents, flavoring agents, coloring agents, and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are suitable disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules.

To prepare hard gelatin capsules, active ingredient may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The agents of this invention may also be administered by non-oral routes. For example, the compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil.

Suitable aqueous vehicles include Ringers solution and isotonic sodium chloride. Such forms will be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses may range from about 1 to 1000 μg/kg/minute of agent, admixed with a pharmaceutical carrier over a period ranging from several minutes to several days.

For topical administration, the agents may be mixed with a pharmaceutical carrier at a concentration of about 0.1% to about 10% of drug to vehicle. Another rhode of administering the agents of the invention may utilize a patch formulation to affect transdermal delivery.

Agents may alternatively be administered in methods of this invention by inhalation, via the nasal or oral routes, e.g., in a spray formulation also containing a suitable carrier.

Exemplary agents useful in methods of the invention will be described by reference to the illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent Unless otherwise specified, the variables are as defined above in reference to Formula I.

Assay Methods:

Preparation of Membranes: CHO-C4 cells expressing recombinant human NPY Y2 receptors were used to prepare membranes for the GTPγS assay. Cells were grown to 80-95% confluency on 15-cm (225 cm$^2$) tissue culture plates. After aspiration of the culture medium, cells were washed twice with 18 ml ice-cold phosphate-buffered saline (PBS), scraped off and suspended in 3 ml ice-cold PBS in pre-cooled centrifuge tubes. The dishes were rinsed with 2 ml ice-old PBS per dish and the washings were combined with the PBS cell suspension from above. Cells pooled from 5-7 dishes were centrifuged for 5 min at 10,000 rpm (12,000 g) in a Sorvall RC5B centrifuge using an SS34 rotor at 40° C. The cell pellet was resuspended in 5 ml ice-cold buffer (20 mM HEPES, 10 mM EDTA; pH 7.4) by vortexing (2-5 sec), homogenized using a Polytron (step 4 for 20-30 sec), and ice-cold buffer added to 25 ml. The suspension was centrifuged again for 20 min at 18,000 rpm (39,000 g) at 4° C. and the pellet resuspended in 5 ml ice-cold buffer (20 mM HEPES, 0.1 mM EDTA; pH 7.4) by vortexing (2-5 sec), homogenized with a Polytron (step 4 for 10 sec), and ice-cold buffer added to 25 ml. The suspension was centrifuged a third time for 20 min at 18,000 rpm (39,000 g) at 4° C. The pellet was resuspend in 1 ml ice-cold buffer (20 mM Hepes, 0.1 mM EDTA; pH 7.4) by vortexing (5-8 sec). Two to five resuspended pellets were combined and homogenized using a Polytron (step 4 for 15-25 sec). A small aliquot (20-50 μl) was removed for protein determination by the Coomassie Plus Protein Assay Reagent (Pierce) using BSA as standard. The membrane suspension was aliquoted in precooled (on dry ice) Eppendorf tubes (0.25-1 ml/tube affording approximately 0.5-2 mg of membrane protein/tube). The pellets were frozen and stored at −80° C.

Scintillation proximity [$^{35}$S]GTPγS binding assay: Frozen membranes from CHO-C4 cells expressing recombinant human NPY Y2 receptors (2 mg for four 96-well plates) were thawed on ice. Thawed membranes were pipetted into 10 ml of assay buffer (20 mM HEPES, 10 mM MgCl2, 100 mM NaCl, pH 7.4) and homogenized briefly using a Polytron. The final assay mixture was prepared in 96-well microtiter plates (Isoplate Wallac, Perkin Elmer). The composition of the assay mixtures in a final volume of 250 μl per well was as follows: 20 mM HEPES, 10 mM MgCl2, 100 mM NaCl, pH 7.4, 30 μM GDP, 1 mg/ml BSA (added fresh), 5 μg membrane protein, 1.5 mg Wheatgerm agglutinin SPA beads (Amersham), 0.45 nM [$^{35}$S]GTPγS (Amersham, SJ1308, 1000 Ci/mmol, stabilized solution), and the test compounds (agonists and/or antagonists) at the appropriate concentrations. The samples were incubated at room temperature for 90 min by shaking, after which the SPA beads were sedimented by centrifugation in an Eppendorf 5804 centrifuge at 2700 rpm for 10 min at room temperature. After 60 min the plates were counted in a TopCount (Canberra). Basal [$^{35}$S]GTPγS binding was measured in the absence of agonist (NPY). Nonspecific binding was measured in the presence of excess (10 μM) unlabelled GTPγS (Sigma). Nonspecific binding never exceeded 10% of basal binding and was thus not subtracted from the experimental data. Antagonists were tested for the inhibition of 0.5 nM NPY-stimulated [$^{35}$S]GTPγS binding. Antagonist inhibition curves were analyzed by non-linear regression using GraphPad Prism software (Version 4.0, GraphPad Software Inc., CA, USA).

In order to illustrate the invention, the following examples are included. These examples do not limit the invention. They are only meant to suggest a method of practicing the invention. Those skilled in the art may find other methods of practicing the invention, which are obvious to them. However, those methods are deemed to be within the scope of this invention. Unless otherwise noted, the materials used in the examples were obtained from readily available commercial sources or synthesized by standard methods known to those skilled in the art.

Flash Chromatography System
  ISCO System, CombiFlash Companion; IG Instrumenten-Gesellschaft AG. Cartusch System.

LC-MS System (Analytical)
  Agilent 1100 Series ; Waters SunFire C18 Column;
  A=Water+0.05% TFA; B=Acetonitrile+0.05% TFA
  Flow: 1.5 ml/Min.

| Rt in min. | % B |
|---|---|
| 0 | 5 |
| 0.3 | 5 |
| 3.3 | 95 |
| 4.3 | 95 |
| 4.5 | 5 |
| 5 | 5 |

Preparative HPLC
Gilson Trilution LC

Method 1
Column: SunFire C18, 30×100 mm, 5 um
Eluent: Water (+0.1% TFA): acetonitrile (+0.1% TFA) from 95:5 to 0:100 in 20 min; 0:100 for 2 min Method 2
Column: SunFire C18, 30×100 mm, 5 um
Eluent: Water (+0.1% TFA) : acetonitrile (+0.1% TFA) from 80:20 to 50:50 in 16 min; 0:100 for 2 min Method 3
Column: SunFire C18, 30×100 mm, 5 um
Eluent: Water (+0.1% TFA) : acetonitrile (+0.1% TFA) from 70:30 to 50:50 in 20 min; 0:100 for 2 min

EXAMPLE 1

(+/−)-N-(1,2-Dimethyl-propyl)-4-[2-(2-methyl-5-oxo-4,4-diphenyl-4,5-dihydro-imidazol-1-yl)-acetyl]-benzamide 4-[2-(2-Methyl-5-oxo-4,4-diphenyl-4,5-dihydro-imidazol-1-yl)-acetyl]-benzoic acid (120 mg, 0.29 mmol) and (+/−)-3-methyl-2-butylamine (45 uL, 0.44 mmol) and N,N'-dicyclohexylcarbodiimide (97 mg, 0.47 mmol) and 4-(dimethylamino)-pryridine (58 mg, 0.47 mmol) are dissolved in 5 mL methylene chloride. The reaction mixture is stirred for 12 hours, filtrated and the filtrate evaporated. The residue of the filtrate is purified by preparative HPLC (Method 1) to yield (+/−)-N-(1,2-dimethyl-propyl)-4-[2-(2-methyl-5-oxo-4,4-diphenyl-4,5-dihydro-imidazol-1-yl)-acetyl]-benzamide (68 mg, 48%). LCIMS at 354 nm; [M+H] 482; Rt 3.304 min.

4-[2-2-Methyl-5-oxo-4,4-diphenyl-4,5-dihydro-imidazol-1-yl)-acetyl]-benzoic acid is prepared as follows:

4-[2-(2-Methyl-5-oxo-4,4-diphenyl-4,5-dihydro-imidazol-1-yl)-acetyl]-benzoic acid ethyl ester To a mixture of 4-(2-bromo-acetyl)-benzoic acid ethyl ester (812 mg, 3 mmol) and 2-methyl-5,5-diphenyl-3,5-dihydro-imidazol-4-one (750 mg, 3 mmol) in 12 mL acetone, potassium carbonate (502 mg, 3.6 mmol) is added and the reaction mixture is heated at 70° C. for 5 min in the microwave oven (Biotage Initiator). The mixture is cooled to room temperature, filtered and the filtrate evaporated to yield the crude product which is subjected to flash chromatography. ISCO Companion CombiFlash, 80 g silica gel, cyclohexane/ethyl acetate, gradient, ethyl acetate 0-100% to yield 4-[2-(2-methyl-5-oxo-4,4-diphenyl4,5-dihydro-imidazol-1-yl)-acetyl]-benzoic acid ethyl ester (635 mg, 45%) as light yellow solid. LC/MS at 254 nm; [M+H] 441; Rt 3.613 min.

4-[2-(2-Methyl-oxo-4,4-diphenyl-4,5-dihydroimidazol-1-yl)acetyl]-benzoic acid

4-[2-(2-Methyl-5-oxo-4,4-diphenyl4,5-dihydro-imidazol-1-yl)-acetyl]-benzoic acid ethyl ester (540 mg, 1.2 mmol) is dissolved in 12 mL dioxane and an aqueous 2 Molar LiOH solution (920 uL, 1.8 mmol) is added drop wise. The reaction mixture is stirred at room temperature for 12 hours. Subsequently the mixture is evaporated and the residue taken up in water. The mixture is stirred and concentrated hydrochloric acid is added drop wise until a pH of 2 is reached. The precipitating crystals are filtered off, re-crystallized from methylene chloride and dried to yield 4-[2-2-methyl-5-oxo-4,4-diphenyl-4,5-dihydro-imidazol-1-yl)-acetyl]-benzoic acid (435 mg, 84%) light yellow solid. LC/MS at 254 nm; [M+H] 413; Rt 3.154 min.

EXAMPLE 2

N-Cyclopentyl-4-[2-(2-methyl-5-oxo-4,4-diphenyl-4,5-dihydro-imidazol-1-yl)-acetyl]-benzamide Synthesis in analogy to Example 1 with cyclopentyl amine to yield N-cyclopentyl-4-[2-(2-methyl-5-oxo-4,4-diphenyl-4,5-dihydro-imidazo-1-yl)-acetyl]-benzamide. LC/MS at 254 nm; [M+H] 480; Rt 3.240 min.

EXAMPLE 3

N,N-Diethyl-4-[2-(2-methyl-5-oxo-4,4-diphenyl-4,5-dihydro-imidazol-1-yl)-acetyl]-benzamide Synthesis in analogy to Example 1 with diethyl amine to yield N,N-diethyl-4-[2-(2-methyl-5-oxo-4,4-diphenyl-4,5-dihydro-imidazol-1-yl)-acetyl]-benzamide. LC/MS at 254 nm; [M+H] 468; Rt 3.149.

EXAMPLE 4

2-Ethyl-N-{4-[2-(2-methyl-5-oxo-4,4-diphenyl-4,5-dihydro-imidazol-1-yl)ethyl]-phenyl}-butyramide 3-[2-(4-Amino-phenyl)-ethyl]-2-methyl-5,5-diphenyl-3,5-dihydro-imidazol-4-one (56 mg, 0.15 mmol) is dissolved in 10 mL methylene chloride and 2-ethyl-butyric acid (18 mg, 0.15 mmol), bromo-tris-pyrrolidino-phosphonium hexafluorophosphate (113 mg, 0.24 mmol) and ethyl diisopropyl amine (42 uL, 0.24 mmol) are added. The mixture is stirred and heated to 50° C. for 5 hours. Subsequently water and methylene chloride are added the organic phase is separated, dried and evaporated. The residue is purified by preparative HPLC (Method 1) to yield 2-ethyl-N-{4-[2-(2-methyl-5-oxo-4,4-diphenyl-4,5-dihydro-imidazol-1-yl)-ethyl]-phenyl}-butyramide (25 mg, 35%). LC/MS at 254 nm; [M+H] 468; Rt 3.351.

3-[2-(4-Amino-phenyl)-ethyl]-2-methyl-5,5-diphenyl-3,5-dihydro-imidazol-4-one is prepared as follows 2-Methyl-3-[2-(4-nitro-phenyl)-ethyl]-5,5-diphenyl-3,5-dihydro-imidazol-4-one 2-Methyl-5,5-diphenyl-3,5-dihydro-imidazol-4-one (1 g, 4 mmol) and 1-(2-bromo-ethyl)-4-nitro-benzene (919 mg, 4 mmol) and potassium carbonate (669 mg, 4.8 mmol) are dissolved in 12 mL acetone and the reaction mixture is heated at 70° C. for 5 min in the microwave oven (Biotage Initiator) and again heated for 5 min at 120° C. The mixture is cooled to room temperature, filtered and the filtrate evaporated to yield the crude product which is subjected to flash chromatography. ISCO Companion CombiFlash, 80 g silica gel, cyclohexane/ethyl acetate, followed by a second purification step, 40 g silica gel, acetone/cylohexane to yield 2-methyl-3-[2-(4-nitro-phenyl)-ethyl]-5,5-diphenyl-3,5-dihydro-imidazol-4-one (750 mg, 45%). LC/MS at 254 nm; [M+H] 400; Rt 3.391 min.

3-[2-4-Amino-phenyl)-ethyl]-2-methyl-5,5-diphenyl-3,5-dihydro-imidazol-4-one

A mixture of 2-methyl-3-[2-(4-nitro-phenyl)-ethyl]-5,5-diphenyl-3,5-dihydro-imidazol-4-one (205 mg, 0.5 mmol) and SnCl$_2$.2H$_2$O (591 mg, 2.6 mmol) in 10 mL ethanol is heated to 50° C. for 5 hours. The reaction mixture is cooled to room temperature, diluted with water and aqueous ammonia is added to reach pH 8-9. The mixture is filtered, the filtrate evaporated and the residue purified by flash chromatography. ISCO Companion CombiFlash, 12 g silica gel, methylene chloride/ethanol to yield 3-[2-(4-amino-phenyl)-ethyl]-2-methyl-5,5-diphenyl-3,5-dihydro-imidazol-4-one (180 mg, 85%). LC/MS at 254 nm; [M+H] 370; Rt 2.424 min.

EXAMPLE 5

3-Methyl-N-{4-[2-(2-methyl-5-oxo-4,4-diphenyl-4,5-dihydro-imidazol-1-yl)-ethyl]-phenyl}-butyramide Synthesis in analogy to Example 4 with 3-methyl-butyric acid to yield 3-methyl-N-4-[2-(2-methyl-5-oxo-4,4-diphenyl-4,5-dihydro-imidazol-1-yl)-ethyl]-phenyl)butyramide. LC/MS at 254 nm; [M+H] 454; Rt 3.079 min.

EXAMPLE 6

(+/−)-1-(3,5-Dimethyl-isoxazol-4-yl)-3-{4-[2-(2-methyl-5-oxo-4-phenyl-4-propyl-4,5-dihydro-imidazol-1-yl)-acetyl]-phenyl}-urea A mixture of (+/−)-3-[2-(4-amino-phenyl)-2-oxo-ethyl]-2-methyl-5-phenyl-5-propyl-3,5-dihydro-imidazol-4-one (88 mg, 0.25 mmol) and 4-isocyanato-3,5-dimethyl-isoxazole (35 mg, 0.25 mmol) in 3 mL dichloromethane is stirred at room temperature for 18 hours. Subsequently the solvent is evaporated and the residue is dissolved in acetonitrile, the solution filtrated and subjected to preparative HPLC purification (method 3) to yield (+/−)-1-(3,5-dimethyl-isoxazol-4-yl)-3-{4-[2-(2-methyl-5-oxo-4-phenyl-4-propyl-4,5-dihydro-imidazol-1-yl)-acetyl]-phenyl}-urea (43 mg, 35%), LC/MS at 254 nm; [M+H] 488; Rt 2.648 min.

(+/−)-3-[2-(4-amino-phenyl)-2-oxo-ethyl]-2-methyl-5-phenyl-5-propyl-3,5-dihydro-imidazol-4-one is prepared as follows:

(+/−)-2-Methyl-3-[2-4-nitro-phenyl)-2-oxo-ethyl]-6-phenyl-5-propyl-3,5-dihydro-imidazol-4-one (+/−)-2-Methyl-5-phenyl-5-propyl-3,5-dihydro-imidazol-4-one (541 mg, 2.5 mmol) and 2-bromo-1-(4-nitro-phenyl)-ethanone (707 mg, 2.8 mmol) and potassium carbonate (698 mg, 5 mmol) are dissolved in 5 mL acetone and the reaction mixture is heated at 70° C. for 10 min in the microwave oven (Biotage Initiator). The mixture is cooled to room temperature filtered and the filtrate evaporated. The residue is subjected to flash chromatography (cyclohexane/ethyl acetate-gradient, ethyl acetate 0-100% in 20 min) to yield (+/−)-2-methyl-3-[2-(4-nitro-phenyl)-2-oxo-ethyl]-5-phenyl-5-propyl-3,5-dihydro-imidazol-4-one (528 mg, 56%). LC/MS at 254 nm; [M+H] 380; Rt 2.959 min.

(+/−)-3-[2-(4-Amino-phenyl)-2-oxo-ethyl]-2-methyl-5-phenyl-5-propyl-3,5-dihydro-imidazol-4-one A mixture of (+/−)-2-methyl-3-[2-(4-nitro-phenyl)-2-oxo-ethyl]-5-phenyl-5-propyl-3,5-dihydro-imidazol-4-one (528 mg, 1.4 mmol) and SnCl$_2$.2H$_2$O (1.92 g, 8.4 mmol) in 15 mL ethanol is heated to 80° C. for 2 hours. The reaction mixture is poured on to 1M sodium hydroxide solution and extracted with ethyl acetate. The combined organic phases are tried and evaporated to yield (+/−)-3-[2-(4-amino-phenyl)-2-oxo-ethyl]-2-methyl-5-phenyl-5-propyl-3,5-dihydro-imidazol-4-one (475 mg, 97%). LCIMS at 254 nm; [M+H] 350; Rt 2.506 min.

EXAMPLE 7

(+/−)-1-(3,5-Dimethyl-isoxazol-4-yl)-3-(4-{2-[4-(4-fluoro-phenyl)-2-methyl-5-oxo-4-propyl-4,5-dihydro-imidazol-1-yl]-acetyl}-phenyl)urea Synthesis in analogy to Example 6 starting with (+/−)-5-(4-fluoro-phenyl)-2-methyl-5-propyl-3,5-dihydro-imidazol-4-one to yield (+/−)-1-(3,5-dimethyl-isoxazol-4-yl)-3-(4-{2-[4-(4-fluoro-phenyl)-2-methyl-5-oxo-4-propyl-4,5-dihydro-imidazol-1-yl]-acetyl}-phenyl) urea. LC/MS at 254 nm [M+H] 506; Rt 2.795 min.

EXAMPLE 8

(+/−)-2-Ethyl-N-{4-[2-(2-methyl-5-oxo-4-phenyl-4-propyl-4,5-dihydro-imidazol-1-yl)-acetyl]-phenyl}-butyramide Synthesis in analogy to Example 6 to yield (+/−)-3-[2-(4-amino-phenyl)-2-oxo-ethyl]-2-methyl-5-phenyl-5-propyl-3,5-dihydro-imidazol-4-one (88 mg, 0.25 mmol), which is dissolved in 2 mL dichloromethane and 70 uL triethyl amine. 2-Ethyl-butyryl chloride (35 uL, 0.25 mmol) is added to the reaction mixture and stirred at room temperature for 18 hours. Subsequently the solvents are evaporated and the residue is dissolved in acetonitrile. The solution is filtrated and subjected to preparative HPLC purification (method 3) to yield (+/−)-2-ethyl-N-{4-[2-(2-methyl-5-oxo-4-phenyl-4-propyl-4,5-dihydro-imidazol-1-yl)-acetyl]-phenyl}-butyramide (39 mg, 35%) LC/MS at 254 nm; [M+H] 448; Rt 2.981 min.

EXAMPLE 9

(+/−)-2-Ethyl-N-(4-{2-[4-(4-fluoro-phenyl)-2-methyl-5-oxo-4-propyl-4,5-dihydro-imidazol-1-yl]-acetyl}-phenyl)-butyramide Synthesis in analogy to Example 6 and Example 8 starting with (+/−)-5-(4-fluoro-phenyl)-2-methyl-5-propyl-3,5-dihydro-imidazol-4-one to yield (+/−)-2-ethyl-N-4-{2-[4-(4-fluoro-phenyl)-2-methyl-5-oxo-4-propyl-4,5-dihydro-imidazol-1-yl]-acetyl}-phenyl)-butyramide. LC/MS at 254 nm; [M+H] 466; Rt 3.130 min.

EXAMPLE 10

(+/−)-1-(3,5-Dimethyl-isoxazol-4-yl)-3-{3-fluoro-4-[2-(2-methyl-5-oxo-4-phenyl-4-propyl-4,5-dihydro-imidazol-1-yl)-acetyl]-phenyl}-urea A mixture of (+/−)-3-[2-(4-amino-2-fluoro-phenyl)-2-oxo-ethyl]-2-methyl-5-phenyl-5-propyl-3,5-dihydro-imidazol-4-one (116 mg, 0.25 mmol) and 4-isocyanato3,5-dimethyl-isoxazole (34.5 mg, 0.25 mmol) in 3 mL dichloromethane is stirred at room temperature for 18 hours. Subsequently the solvent is evaporated and the residue is dissolved in acetonitrile, the solution filtrated and subjected to preparative HPLC purification (Method 3) to yield (+/−)-1-(3,5-dimethyl-isoxazol-4-yl)-3-{3-fluoro-4-[2-(2-methyl-5-oxo-4-phenyl-4-propyl-4,5-dihydro-imidazol-1-yl)-acetyl]-phenyl}-urea (44 mg, 35%), LC/MS at 254 nm; [M+H] 506; Rt 2.754 min.

(+/−)-3-[2-(4-amino-2-fluoro-phenyl)-2-oxo-ethyl]-2-methyl-5-phenyl-5-propyl-3,5-dihydro-imidazol-4-one is prepared as follows:

N-[4-(2-Bromo-acetyl)-3-fluoro-phenyl]-acetamide

N-(4-Acetyl-3-fluoro-phenyl)-acetamide (10.2 g, 51.2 mmol) is dissolved in 50 mL chloroform. At room temperature bromine (1.98 mL, 38.4 mmol) is added drop wise. The reaction mixture is stirred at room temperature for 1.5 hours. Subsequently the precipitated product is filtered off, washed first with chloroform and then with ethyl acetate to yield N-[4-(2-bromo-acetyl)-3-fluoro-phenyl]-acetamide (8.7 g, 43%); LCIMS at 254 nm; [M+H] 275; Rt 2.918 min)

N-{3-Fluoro-4-[2-(2-methyl-5-oxo-4-phenyl-4-propyl-4,5-dihydro-imidazol-1-yl)-acetyl]-phenyl}-acetamide To a mixture of N-[4-(2-bromo-acetyl)-3-fluoro-phenyl]-acetamide (1.1 g, 2.8 mmol) and (+/−)-2-methyl-5-phenyl-5-propyl-3,5-dihydro-imidazol-4-one (541 mg, 2.5 mmol) in 5 mL acetone potassium carbonate (698 mg, 5 mmol) is added and the reaction mixture is heated at 70° C. for 10 min in the microwave oven (Biotage Initiator). The mixture is cooled to room temperature, filtered and the filtrate evaporated to yield the crude product which is subjected to flash chromatography. ISCO Companion CombiFlash, 40 g silica gel, cyclohexane/ethyl acetate-gradient, ethyl acetate 0-100% to give (+/−)-N-{3-fluoro-4-[2-(2-methyl-5-oxo-4-phenyl-4-propyl-4,5-dihydro-imidazol-1-yl)-acetyl]-phenyl}-acetamide (956 mg, 71%). LC/MS at 254 nm; [M+H] 410; Rt 2.850 min (+/−)-3-[2-(4-Amino-2-fluoro-phenyl)-2-oxo-ethyl]-2-methyl-5-phenyl-5-propyl-3,5-dihydro-imidazol-4-one (+/−)-N-{3-fluoro-4-[2-(2-methyl-5-oxo-4-phenyl-4-propyl-4,5-dihydro-imidazol-1-yl)-acetyl]-phenyl}-acetamide (956 mg, 1.8 mmol) is dissolved in 10 mL ethanol and concentrated hydrochloric acid (192 uL, 1.9 mmol) is added. The mixture is heated to 100° C. in the microwave oven (Biotage Initiator) for 30 min. Subsequently the solvent is evaporated and the residue is suspended in concentrated sodium hydrogen carbonate solution and dichloromethane. This mixture is extracted three times with dichloromethane. The organic phase is dried with sodium sulfate, filtrated and evaporated to yield (+/−)-3-[2-(4-amino-2-fluoro-phenyl)-2-oxo-ethyl]-2-methyl-5-phenyl-5-propyl-3,5-dihydro-imidazol-4-one (325 mg, 40%) as light brown foam. LC/MS at 254 nm; [M+H] 368; Rt 2.616 min.

EXAMPLE 11

(+/−)-1-(3,5-Dimethyl-isoxazol-4-yl)-3-(3-fluoro-4-{2-[4-(4-fluoro-phenyl)-2-methyl-5-oxo-4-propyl-4,5-dihydro-imidazol-1-yl]acetyl}-phenyl)-urea Synthesis in analogy to Example 10 starting with (+/−)-5-(4-fluoro-phenyl)-2-methyl-5-propyl-3,5-dihydro-imidazol-4-one to yield (+/−)-1-(3,5-dimethyl-isoxazol-4-yl)-3-(3-fluoro-4-{2-[4-(4-fluoro-phenyl)-2-methyl-5-oxo-4-propyl-4,5-dihydro-imidazol-1-yl]acetyl}-phenyl)-urea. LC/MS at 254 nm; [M+H] 524; Rt 2.901 min.

EXAMPLE 12

(+/−)-2-Ethyl-N-{3-fluoro-4-[2-(2-methyl-5-oxo-phenyl-4-propyl-4,5-dihydro-imidazol-1-yl)-acetyl]-phenyl}-butyramide Synthesis in analogy to Example 10 and Example 8 to yield (+/−)-2-ethyl-N-{3-fluoro4-[2-(2-methyl-5-oxo-4-phenyl-4-propyl-4,5-dihydro-imidazol-1-yl)-acetyl]-phenyl}-butyramide. LC/MS at 254 nm; [M+H] 466; Rt 3.097 min.

EXAMPLE 13

(+/−)-2-Ethyl-N-(3-fluoro-4-{2-[4-(4-fluoro-phenyl)-2-methyl-5-oxo-4-propyl-4,5-dihydro-imidazol-1-yl]-acetyl}-phenyl)-butyramide Synthesis in analogy to Example 12 starting with (+/−)-5-(4-fluoro-phenyl)-2-methyl-5-propyl-3,5-dihydro-imidazol-4-one to yield (+/−)-2-ethyl-N-(3-fluoro-4-{2-[4-(4-fluoro-phenyl)-2-methyl-5-oxo-4-propyl-4,5-dihydro-imidazol-1-yl]-acetyl}phenyl)-butyramide. LC/MS at 254 nm; [M+H] 484; Rt 3.439 min.

EXAMPLE 14

Tetrahydro-furan-3-carboxylic acid (34-fluoro-4-{2-[4-(4-fluoro-phenyl)-2-methyl-5-oxo-propyl-4,5-dihydro-imidazol-1-yl]-acetyl}-phenyl)-amide Synthesis in analogy to Example 13 with tetrahydro-furan-3-carbonyl chloride to yield tetrahydro-furan-3-carboxylic acid (3-fluoro4-{2-[4-(4-fluoro-phenyl)-2-methyl-5-oxo-4-propyl-4,5-dihydro-imidazol-1-yl]-acetyl}-phenyl)-amide. LC/MS at 254 nm; [M+H] 484; Rt 3.048 min.

EXAMPLE 15

Tetrahydro-furan-3-carboxylic acid {3-fluoro-4-[2-(2-methyl-5-oxo-4-phenyl-4-propyl-4,5-dihydro-imidazol-1yl)-acetyl]-phenyl}-amide Synthesis in analogy to Example 14 starting with 2-methyl-5-phenyl-5-propyl-3,5-dihydro-imidazol-4-one to yield tetrahydro-furan-3-carboxylic acid {3-fluoro-4-[2-(2-methyl-5-oxo-4-phenyl-4-propyl-4,5-dihydro-imidazol-1-yl)-acetyl]-phenyl}amide. LC/MS at 254 nm; [M+H] 466; Rt 2.709 min.

EXAMPLE 16

Tetrahydro-furan-3-carboxylic acid (4-{2-[4-(4-fluoro-phenyl)-2-methyl-5-oxo-4-propyl-4,5-dihydro-imidazol-1-yl]-acetyl}-phenyl)-amide Synthesis in analogy to Example 9 and Example 15 to yield tetrahydro-furan-3-carboxylic acid (4-{2-[4-(4-fluoro-phenyl)-2-methyl-5-oxo-4-propyl-4,5-dihydro-imidazol-1-yl]-acetyl}-phenyl)-amide. LC/MS at 254 nm; [M+H] 466; Rt 2.942min.

EXAMPLE 17

(+/−)-2-(3,5-Dimethyl-isoxazol-4-yl)-N-fluoro-4-{2-[4-(4-fluoro-phenyl)-2-methyl-5-oxo-4-propyl-4,5-dihydro-imidazol-1-yl]-acetyl}-phenyl)-acetamide Synthesis in analogy to Example 14 and Example 1 starting from (+/−)-3-[2-4-amino2-fluoro-phenyl)-2-oxo-ethyl]-5-(4-fluoro-phenyl)-2-methyl-5-propyl-3,5-dihydro-imidazol-4-one and (3,5-dimethylisoxazol-4-yl)-acetic acid to yield (+/−)-2-3,5-dimethyl-isoxazol-4-yl)-N-(3-fluoro-4-{2-[4-(4-fluoro-phenyl)-2-methyl-5-oxo-4-propyl-4,5-dihydro-imidazol-1-yl]-acetyl}-phenyl)-acetamide. LC/MS at 254 nm; [M+H] 523; Rt 3.272 min.

EXAMPLE 18

(+/−)-1-(3,6-Dimethylisoxazol-4-yl)-3-(3-fluoro-4-{2-[4-4-fluoro-phenyl)-2-methyl-5-oxo-4-propyl-4,5-dihydro-imidazol-1-yl]-acetyl}-phenyl)-1,3-dimethyl-urea Synthesis in analogy to Example 7 and Example 10 starting from (+/−)-3-[2-(4-amino-2-fluoro-phenyl)-2-oxo-ethyl]-5-(4-fluoro-phenyl)-2-methyl-5-propyl-3,5-dihydro-imidazol-4-one and 4-isocyanato-3,5-dimethyl-isoxazole to yield (+/−)-1-(3,5-dimethyl-isoxazol-4-yl)-3-(3-fluoro-4-{2-[4-(4-fluoro-phenyl)-2-methyl-5-oxo-4-propyl-4,5-dihydro-imidazol-1-yl]-acetyl}-phenyl)-urea. The compound is suspended in a 1 molar aqueous sodium hydroxide solution. Subsequently iodomethane (1 equivalent) and tetrabutyl ammonium chloride (1 equivalent) are added and the mixture is stirred for 18 hours at room temperature. Subsequently the product is extracted with dichloromethane and subjected to preparative LC purification (method 3) to yield (+/−)-1-(3,5-dimethyl-isoxazol-4-yl)-3-(3-fluoro-4-{2-[4-(4-fluoro-phenyl)-2-methyl-5-oxo-4-propyl-4,5-dihydro-imidazol-1-yl]-acetyl}-phenyl)-1,3-dimethyl-urea LC/MS at 254 nm; [M+H] 552; Rt 3.502 min.

EXAMPLE 19

2-(2,4-Dimethoxy-phenyl)-N-{4-[1-hydroxy-2-(2-methyl-5-oxo-4,4-diphenyl-4,5-dihydro-imidazol-1-yl)-ethyl]-phenyl}-acetamide Synthesis in analogy to Example 8 starting from 3-[2-(4-amino-phenyl)-2-oxo-ethyl]-2-methyl-5,5-diphenyl-3,5-dihydro-imidazol-4-one and (2,4-dimethoxy-phenyl)-acetyl chloride to yield 2-(2,4-dimethoxy-phenyl)-N-{4-[2-(2-methyl-5-oxo-4,4-diphenyl-4,5-dihydro-imidazol-1-yl)-acetyl]-phenyl}-acetamide (55 mg, 0.098 mmol) which is dissolved 5 mL dry ethanol. Subsequently LiBH$_4$ (22.5 mg, 0.98 mmol) is added and the reaction mixture is stirred for 4 hour at reflux temperature. The reaction is then diluted with 5 mL water and the solvents evaporated. The residue is purified by preparative HPLC (method 3) to yield 2-(2,4-dimethoxy-phenyl)-N-{4-[1-hydroxy-2-(2-methyl-5-oxo-4,4-diphenyl-4,5-dihydro-imidazol-1-yl)-ethyl]-phenyl}-acetamide (15 mg, 27%). LC/MS at 254 nm; [M+H] 565; Rt=3.006 min.

EXAMPLE 20

N-{4-[1-Hydroxy-2-(2-methyl-5-oxo-4,4-diphenyl-4,5-dihydro-imidazol-1-yl)-ethyl]-phenyl}-2-(2-methoxy-phenyl)-acetamide Synthesis in analogy to Example 8 and Example 19 starting from 3-[2-(4-amino-phenyl)-2-oxo-ethyl]-2-methyl-5,5-diphenyl-3,5-dihydro-imidazol-4-one and (2-methoxy-phenyl)-acetyl chloride to yield N-{4-[1-hydroxy-2-(2-methyl-5-oxo-4,4-diphenyl-4,5-dihydro-imidazol-1-yl)-ethyl]-phenyl}-2-(2-methoxy-phenyl)-acetamide. LC/MS at 254 nm; [M+H] 535: Rt=3.003 min.

EXAMPLE 21

2-Fluoro-N-{4-[2-(2-methyl-5-oxo-4,4-diphenyl-4,5-dihydro-imidazol-1-yl)-acetyl]-phenyl}-benzamide Synthesis in analogy to Example 8 starting from 3-[2-(4-amino-phenyl)-2-oxo-ethyl]-2-methyl-5,5-diphenyl-3,5-dihydro-imidazol-4-one and 2-fluoro-benzoyl chloride to yield 2-fluoro-N-{4-[2-(2-methyl-5-oxo-4,4-diphenyl-4,5-dihydro-imidazol-1-yl)-acetyl]-phenyl}-benzamide. LC/MS at 254 nm; [M+H] 506; Rt 3.438 min.

EXAMPLE 22

N-{4-[2-(2-Methyl-5-oxo-4,4-diphenyl-4,5-dihydro-imidazol-1-yl)-acetyl]-phenyl}-2-o-tolyl-acetamide Synthesis in analogy to Example 8 starting from 3-[2-(4-amino-phenyl)-2-oxo-ethyl]-2-methyl-5,5-diphenyl-3,5-dihydro-imidazol-4-one and o-tolyl-acetyl chloride to yield N-{4-[2-(2-methyl-5-oxo-4,4-diphenyl-4,5-dihydro-imidazol-1-yl)-acetyl]-phenyl}-2-o-tolyl-acetamide. LC/MS at 254 nm; [M+H] 516; Rt 3.526 min.

EXAMPLE 23

2-Methoxy-N-{4-[2-(2-methyl-5-oxo-4,4-diphenyl-4,5-dihydro-imidazol-1-yl)-acetyl]-phenyl}-benzamide Synthesis in analogy to Example 8 starting from 3-[2-(4-amino-phenyl)-2-oxo-ethyl]-2-methyl-5,5-diphenyl-3,5-dihydro-imidazol-4-one and 2-methoxy-benzoyl chloride to yield 2-methoxy-N-{4-[2-(2-methyl-5-oxo-4,4-diphenyl-4,5-dihydro-imidazol-1-yl)-acetyl]-phenyl}-benzamide. LC/MS at 254 nm; [M+H] 518; Rt 3.772 min.

EXAMPLE 24

(−)-2-Ethyl-N-{4-[2-(2-methyl-5-oxo-4-phenyl-4-propyl-4,5-dihydro-imidazol-1-yl)-acetyl]-phenyl}-butyramide Synthesis in analogy to Example 8 starting from enantiomerically pure 3-[2-(4-amino-phenyl)-2-oxo-ethyl]-2-methyl-5-phenyl-5-propyl-3,5-dihydro-imidazol-4-one and 2-ethyl-butyryl chloride to yield (−)-2-ethyl-N-{4-[2-(2-methyl-5-oxo-4-phenyl-4-propyl-4,5-dihydro-imidazol-1-yl)-acetyl]-phenyl}-butyramide. LC/MS at 254 nm; [M+H] 448; Rt=3.313 min; optical rotation=−8.2°, c=1.0 in methanol.

EXAMPLE 25

(+)-2-Ethyl-N-{4-[2-2-methyl-5-oxo-4-phenyl-4-propyl-4,5-dihydro-imidazol-1-yl)-acetyl]-phenyl}-butyramide Synthesis in analogy to Example 8 starting from enantiomerically pure 3-[2-(4-amino-phenyl)-2-oxo-ethyl]-2-methyl-5-phenyl-5-propyl-3,5-dihydro-imidazol-4-one and 2-ethyl-butyryl chloride to yield (+)-2-ethyl-N-{4-[2-(2-methyl-5-oxo-4-phenyl-4-propyl-4,5-dihydro-imidazol-1-yl)-acetyl]-phenyl}-butyramide. LC/MS at 254 nm; [M+H] 448; Rt=3.506 min; optical rotation=+8.3°, c=1.0 in methanol.

EXAMPLE 26

(+/−)-2-Ethyl-N-{4-[1-hydroxy-2-(2-methyl-5-oxo-4,4-diphenyl-4,5-dihydro-imidazol-1-yl)-ethyl]-phenyl}-butyramide Synthesis in analogy to Example 19 starting from 3-[2-(4-amino-phenyl)-2-oxo-ethyl]-2-methyl-5,5-diphenyl-3,5-dihydro-imidazol-4-one and 2-ethyl-butyryl chloride to yield (+/−)-2-ethyl-N-{4-[1-hydroxy-2-(2-methyl-5-oxo-4,4-diphenyl-4,5-dihydro-imidazo-1-yl)-ethyl]-phenyl}-butyramide. LC/MS at 254 nm; [M+H] 484; Rt 3.032 min.

EXAMPLE 27

1-(3,5-Dimethyl-isoxazol-4-yl)-3-{4-[2-(2-methyl-5-oxo-4,4-diphenyl-4,5-dihydro-imidazol-1-yl)-acetyl]-phenyl}-urea Synthesis in analogy to Example 6 starting from 3-[2-(4-amino-phenyl)-2-oxo-ethyl]-2-methyl-5,5-diphenyl-3,5-dihydro-imidazol-4-one and 4-isocyanato-3,5-dimethyl-isoxazole to yield 1-(3,5-dimethyl-isoxazol-4-yl)-3-{4-[2-(2-methyl-5-oxo-4,4-diphenyl-4,5-dihydro-imidazol-1-yl)-acetyl]-phenyl}-urea. LC/MS at 254 nm; [M+H] 522; Rt 3.191 min.

EXAMPLE 28

2-(2,4-Dimethoxy-phenyl)-N-{4-[2-(2-methyl-5-oxo-4,4-diphenyl-4,5-dihydro-imidazol-1-yl)-acetyl]-phenyl}-acetamide Synthesis in analogy to Example 8 starting from 3-[2-(4-amino-phenyl)-2-oxo-ethyl]-2-methyl-5,5-diphenyl-3,5-dihydro-imidazol-4-one and (2,4-dimethoxy-phenyl)-acetyl chloride to yield 2-(2,4-dimethoxy-phenyl)-N-{4-[2-(2-methyl-5-oxo-4,4-diphenyl-4,5-dihydro-imidazol-1-yl)-acetyl]-phenyl}-acetamide. LC/MS at 254 nm; [M+H] 562; Rt 3.533 min.

EXAMPLE 29

2-3,5-methyl-isoxazol-4-yl)-N-{4-[2-(2-methyl-5-oxo-4,4-diphenyl-4,5-dihydro-imidazol-1-yl)-acetyl]-phenyl}-acetamide Synthesis in analogy to Example 17 starting from 3-[2-(4-amino-phenyl)-2-oxo-ethyl]-2-methyl-5,5-diphenyl-3,5-dihydro-imidazol-4-one and (3,5-dimethyl-isoxazol-4-yl)-acetyl chloride to yield 2-(3,5-dimethyl-isoxazol-4-yl)-N-{4-[2-(2-methyl-5-oxo-4,4-diphenyl-4,5-dihydro-imidazol-1-yl)-acetyl]-phenyl}-acetamide. LC/MS at 254 nm; [M+H] 521; Rt 3,083 min.

EXAMPLE 30

2-(2-Methoxy-phenyl)-N-{4-[2-(2-methyl-5-oxo-4,4-phenyl-4,5-dihydro-imidazol-1yl)-acetyl]-phenyl}-acetamide Synthesis in analogy to Example 8 starting from 3-[2-(4-amino-phenyl)-2-oxo-ethyl]-2-methyl-5,5-phenyl-3,5-dihydro-imidazol-4-one and (2-methoxy-phenyl)-acetyl chloride to yield 2-(2-methoxy-phenyl)-N-{4-[2-(2-methyl-5-oxo-4,4-diphenyl-4,5-dihydro-imidazol-1-yl)-acetyl]-phenyl}-acetamide. LC/MS at 254 nm; [M+H] 532; Rt 3.356 min.

EXAMPLE 31

1-(2-Fluoro-phenyl)-3-{4-[2-(2-methyl-5-oxo-4,4-diphenyl-4,5-dihydro-imidazol-1-yl)-acetyl]-phenyl}-urea Synthesis in analogy to Example 6 starting from 3-[2-(4-amino-phenyl)-2-oxo-ethyl]-2-methyl-5,5-diphenyl-3,5-dihydro-imidazol-4-one and 1-fluoro-2-isocyanato-benzene to yield 1-(2-fluoro-phenyl)-3-{4-[2-(2-methyl-5-oxo-4,4-diphenyl-4,5-dihydro-imidazol-1-yl)-acetyl]-phenyl}-urea. LC/MS at 254 nm; [M+H] 521; Rt 3.641 min.

EXAMPLE 32

1-{4-[2-(2-Methyl-5-oxo-4,4-diphenyl-4,5-dihydro-imidazol-1-yl)-acetyl]-phenyl}-3-(4-nitro-phenyl)-urea Synthesis in analogy to Example 6 starting from 3-[2-(4-amino-phenyl)-2-oxo-ethyl]-2-methyl-5,5-diphenyl-3,5-dihydro-imidazol-4-one and 1-isocyanato-4-nitro-benzene to yield 1-{4-[2-(2-methyl-5-oxo-4,4-diphenyl-4,5-dihydro-imidazol-1-yl)-acetyl]-phenyl}-3-(4-nitro-phenyl)-urea. LC/MS at 254 nm; [M+H] 548; Rt 3.601 min.

EXAMPLE 33

2-Ethyl-N-{3-fluoro-4-[2-(2-methyl-5-oxo-4,4-diphenyl-4,5-dihydro-imidazol-1-yl)-acetyl]-phenyl}-butyramide Synthesis in analogy to Example 8 and Example 10 starting from 3-[2-(4-amino-2-fluoro-phenyl)-2-oxo-ethyl]-2-methyl-5,5-diphenyl-3,5-dihydro-imidazol-4-one and 2-ethyl-butyryl chloride to yield 2-ethyl-N-{3-fluoro4-[2-(2-methyl-5-oxo-4,4-diphenyl-4,5-dihydro-imidazo-1-yl)-acetyl]-phenyl}-butyramide. LC/MS at 254 nm; [M+H] 402; Rt=3.805 min.

EXAMPLE 34

2-Ethyl-N-{4-[2-(2-methyl-5-oxo-4,4-diphenyl-4,5-dihydro-imidazol-1-yl)-acetyl]-phenyl}-butyramide Synthesis in analogy to Example 8 starting from 3-[2-4-amino-phenyl)-2-oxo-ethyl]-2-methyl-5,5-diphenyl-3,5-dihydro-imidazol-4-one and 2-ethyl-butyryl chloride to yield 2-ethyl-N-{4-[2-(2-methyl-5-oxo-4,4-diphenyl-4,5-dihydro-imidazol-1-yl)-acetyl]-phenyl}-butyramide. LC/MS at 254 nm; [M+H] 482; Rt=3.664 min.

EXAMPLE 35

(−)-2-(3,5-Dimethyl-isoxazol-4-yl)-N-(3-fluoro-4-{2-[4-(4-fluoro-phenyl)-2-methyl-5-oxo-4-propyl-4,5-dihydro-imidazol-1-yl]-acetyl}-phenyl)acetamide Synthesis in analogy to Example 14 and Example 1 starting from enantiomerically pure 3-[2-(4-amino-2-fluoro-phenyl)-2-oxo-ethyl]-5-(4-fluoro-phenyl)-2-methyl-5-propyl-3,5-dihydro-imidazol-4-one and (3,5-dimethylisoxazol-4-yl)-acetic acid to yield (−)-2-(3,5-dimethyl-isoxazol-4-yl)-N-(3-fluoro-4-{2-[4-(4-fluoro-phenyl)-2-methyl-5-oxo-4-propyl-4,5-dihydro-imidazol-1-yl]-acetyl}-phenyl)-acetamide. LC/MS at 254 nm; [M+H] 523; Rt 3.417 min; optical rotation $\alpha^D{}_{25}$−1.4°, c=0.5 in methanol.

EXAMPLE 36

(+)-2-(3,5-Dimethyl-isoxazol-4-yl)-N-(3-fluoro-4-{2-[4-(4-fluoro-phenyl)-2-methyl-5-oxo-4-propyl-4,5-dihydro-imidazol-1-yl]-acetyl}-phenyl)-acetamide Synthesis in analogy to Example 14 and Example 1 starting from enantiomerically pure 3-[2-(4-amino-2-fluoro-phenyl)-2-oxo-ethyl]-5-4-fluoro-phenyl)-2-methyl-5-propyl-3,5-dihydro-imidazol-4-one and (3,5-dimethylisoxazol-4-yl)-acetic acid to yield (+)-2-(3,5-dimethyl-isoxazol-4-yl)-N-(3-fluoro-4-{2-[4-(4-fluoro-phenyl)-2-methyl-5-oxo-4-propyl-4,5-dihydro-imidazol-1-yl]-acetyl}-phenyl)-acetamide. LC/MS at 254 nm; [M+H] 523; Rt 3.419 min; optical rotation $\alpha^D{}_{25}$+1.0°, c=0.5 in methanol.

Biological Testing

Antagonistic activity of compounds of the present invention was examined by the Scintillation proximity [$^{35}$S]GTPγS binding assay as described above (inhibition of 0.5 nM NPY-stimulated [$^{35}$S]GTPγS binding). The table below represents percentages of inhibition at a concentration of 10 µM.

| Compound | [%] inhibiton at 10 µM |
|---|---|
| 1 | 34 |
| 4 | 46 |
| 5 | 35 |
| 6 | 99 |
| 7 | 91 |
| 9 | 68 |
| 10 | 97 |
| 11 | 96 |
| 14 | 39 |
| 15 | 42 |
| 16 | 28 |
| 17 | 87 |
| 18 | 70 |
| 21 | 61 |
| 22 | 55 |
| 23 | 46 |
| 25 | 92 |
| 26 | 45 |
| 27 | 100 |
| 30 | 78 |
| 33 | 60 |
| 34 | 65 |
| 35 | 92 |
| 36 | 75 |

The invention claimed is:
1. A compound of the formula I

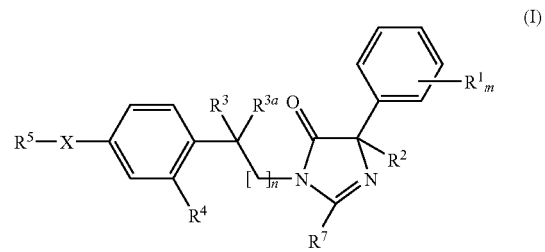

wherein
$R^3$ and $R^{3a}$ together represent oxo (═O) or
$R^3$ represents hydrogen and $R^{3a}$ represents hydroxy or
$R^3$ represents hydrogen and $R^{3a}$ represents hydrogen and
X represents —C(O)—NR$^6$—; —NR$^6$—C(O), —NR$^6$—C(O)—NR$^6$—;
n represents 0, 1 or 2;
m represents 0, 1, 2 or 3;
$R^1$ represents hydrogen or a substituent different from hydrogen;
$R^2$ represents an optionally substituted aryl group, an optionally substituted cycloalkyl group, an optionally substituted heteroaryl group, an optionally substituted heterocyclyl group; an optionally substituted alkyl group;
$R^4$ represents hydrogen or a substituent different from hydrogen;
$R^5$ represents an optionally substituted aryl group, an optionally substituted cycloalkyl group, an optionally substituted heteroaryl group, an optionally substituted heterocyclyl group; an optionally substituted alkyl group;
$R^6$ represents hydrogen, alkyl, cycloalkyl;
$R^7$ represents H, an optionally substituted aryl group, an optionally substituted cycloalkyl group, an optionally substituted alkyl group;
and provided if n represents 0, $R^{3a}$ does not represent hydroxy;
in free base form or in acid addition salt form.
2. The compound of formula I according to claim 1 wherein $R^1$ represents hydrogen, halogen, cyano, nitro, (C$_{1-8}$)alkyl, (C$_{1-8}$)alkyl substituted by halogen, (C$_{3-8}$)cycloalkyl, (C$_{3-8}$)cycloalkyl(C$_{1-8}$)alkyl, (C$_{3-8}$)cycloalkoxy, (C$_{3-8}$)cycloalkoxy(C$_{1-8}$)alkyl, (C$_{3-8}$)cycloalkyl(C$_{1-8}$)alkoxy, (C$_{3-8}$)cycloalkoxy(C$_{1-8}$)alkoxy, aryl, aryl(C$_{1-8}$)alkyl, aryloxy, aryloxy(C$_{1-8}$)alkyl, aryl(C$_{1-8}$)alkoxy, aryloxy(C$_{1-8}$)alkoxy, carboxy, carbamyl, hydroxy, (C$_{1-8}$)alkoxy, (C$_{1-8}$)alkoxy(C$_{1-8}$)alkoxy, (C$_{1-8}$)alkoxy substituted by halogen, (C$_{1-8}$)alkoxy(C$_{1-8}$)alkyl, (C$_{1-8}$)alkylthio, (C$_{1-8}$)alkylthio(C$_{1-8}$)alkyl, (C$_{1-8}$)alkylsulfinyl, (C$_{1-8}$)alkylsulfinyl(C$_{1-8}$) alkyl, (C$_{1-8}$)alkylsulfonyl, (C$_{1-8}$)alkylsulfonyl(C$_{1-8}$)alkyl, amino, (C$_{1-8}$)alkylamino, di(C$_{1-8}$) alkylamino with two identical or different (C$_{1-8}$)alkyl moieties, amino(C$_{1-8}$)alkyl, (C$_{1-8}$)alkylamino(C$_{1-8}$)alkyl, di(C$_{1-8}$)alkylamino(C$_{1-8}$) alkyl with two identical or different (C$_{1-8}$)alkyl moieties in the di(C$_{1-8}$)alkylamino moiety, amino, (C$_{1-8}$)alkoxy, (C$_{1-8}$)alkylamino (C$_{1-8}$)alkoxy, di(C$_{1-8}$)alkylamino (C$_{1-8}$)alkoxy with two identical or different (C$_{1-8}$)alkyl moieties, aminosulfonyl, (C$_{1-8}$)alkylaminosulfonyl, di(C$_{1-8}$)alkylaminosulfonyl with two identical or different (C$_{1-8}$)alkyl moieties, formyl, (C$_{1-8}$)alkylcarbonyl, formyloxy, $(C_{1-8})$alkylcarbonyloxy, formyl$(C_{1-8})$alkyl, $(C_{1-8})$alkylcarbonyl$(C_{1-8})$alkyl, formyl$(C_{1-8})$alkoxy, $(C_{1-8})$alkylcarbonyl$(C_{1-8})$alkoxy, $(C_{1-8})$alkoxycarbonyl, $(C_{1-8})$alkoxycarbonyloxy, $(C_{1-8})$alkoxycarbonyl$(C_{1-8})$alkyl and $(C_{1-8})$alkoxycarbonyl$(C_{1-8})$alkoxy;

$R^2$ represents an aryl group or a $(C_3$-$C_8)$cycloalkyl group or a heterocyclyl group with 3 to 8 ring atoms or a heteroaryl group with 3 to 8 ring atoms or a $(C_1$-$C_8)$alkyl group;

wherein said aryl group, $(C_3$-$C_8)$cycloalkyl group, heteroaryl group, heterocyclyl group is unsubstituted, mono-substituted, di-substituted or tetra-substituted, the optional substituent(s) being independently selected from the group consisting of halogen, cyano, nitro, carboxy, carbamyl, hydroxy, $(C_{1-8})$alkyl, $(C_{1-8})$alkyl substituted by halogen, $(C_{3-8})$cycloalkyl, $(C_{3-8})$cycloalkyl$(C_{1-8})$alkyl, $(C_{3-8})$cycloalkoxy, $(C_{3-8})$cycloalkoxy$(C_{1-8})$alkyl, $(C_{3-8})$cycloalkyl$(C_{1-8})$alkoxy, $(C_{3-8})$cycloalkoxy$(C_{1-8})$alkoxy, aryl, aryl$(C_{1-8})$alkyl, aryloxy, aryloxy$(C_{1-8})$alkyl, aryl$(C_{1-8})$alkoxy, aryloxy$(C_{1-8})$alkoxy, $(C_{1-8})$alkoxy, $(C_{1-8})$alkoxy$(C_{1-8})$alkoxy, $(C_{1-8})$alkoxy substituted by halogen, $(C_{1-8})$alkoxy$(C_{1-8})$alkyl, $(C_{1-8})$alkylthio, $(C_{1-8})$alkylthio$(C_{1-8})$alkyl, $(C_{1-8})$alkylsulfinyl, $(C_{1-8})$alkylsulfinyl$(C_{1-8})$alkyl, $(C_{1-8})$alkylsulfonyl, $(C_{1-8})$alkylsulfonyl$(C_{1-8})$alkyl, amino, $(C_{1-8})$alkylamino, di$(C_{1-8})$alkylamino with two identical or different $(C_{1-8})$alkyl moieties, amino$(C_{1-8})$alkyl, $(C_{1-8})$alkylamino$(C_{1-8})$alkyl, di$(C_{1-8})$alkylamino$(C_{1-8})$alkyl with two identical or different $(C_{1-8})$alkyl moieties in the di$(C_{1-8})$alkylamino moiety, amino$(C_{1-8})$alkoxy, $(C_{1-8})$alkylamino$(C_{1-8})$alkoxy, di$(C_{1-8})$alkylamino$(C_{1-8})$alkoxy with two identical or different $(C_{1-8})$alkyl moieties, formyl, $(C_{1-8})$alkylcarbonyl, formyloxy, $(C_{1-8})$alkylcarbonyloxy, formyl$(C_{1-8})$alkyl, $(C_{1-8})$alkylcarbonyl$(C_{1-8})$alkyl, formyl$(C_{1-8})$alkoxy, $(C_{1-8})$alkylcarbonyl$(C_{1-8})$alkoxy, $(C_{1-8})$alkoxycarbonyl, $(C_{1-8})$alkoxycarbonyloxy, $(C_{1-8})$alkoxycarbonyl$(C_{1-8})$alkyl, $(C_{1-8})$alkoxycarbonyl$(C_{1-8})$alkoxy, —OCH$_2$O—, —C(=O)OCH$_2$—, —CH$_2$O C(=O)— and —CH=CHCH=CH—, the four last-mentioned optional substituents in each case being attached to two adjacent ring carbon atoms of the said moiety and wherein said $(C_{1-8})$alkyl group is unsubstituted or mono-, di-, tri or tetra-substituted, the optional substituent(s) on the said $(C_{1-8})$alkyl moiety being independently selected from the group consisting of halogen, cyano, oxo, nitro, amino, $(C_{1-8})$alkoxy, $(C_{1-8})$alkoxy$(C_{1-8})$alkoxy, $(C_{1-8})$alkylthio, $(C_{1-8})$alkylsulfinyl, $(C_{1-8})$alkylsulfonyl, $(C_{1-8})$alkylcarbonyloxy, $(C_{1-8})$alkoxycarbonyl and $(C_{1-8})$alkoxycarbonyloxy, $(C_{3-8})$cycloalkyl, $(C_{3-8})$cycloalkyl$(C_{1-8})$alkyl, $(C_{3-8})$cycloalkoxy, $(C_{3-8})$cycloalkoxy$(C_{1-8})$alkyl, $(C_{3-8})$cycloalkyl$(C_{1-8})$alkoxy, $(C_{3-8})$cycloalkoxy$(C_{1-8})$alkoxy, aryl, aryl$(C_{1-8})$alkyl, aryloxy, aryloxy$(C_{1-8})$alkyl, aryl$(C_{1-8})$alkoxy, aryloxy$(C_{1-8})$alkoxy, carboxy, carbamyl, hydroxy, $(C_{1-8})$alkoxy, $(C_{1-8})$alkoxy$(C_{1-8})$alkoxy, $(C_{1-8})$alkoxy substituted by halogen, $(C_{1-8})$alkoxy$(C_{1-8})$alkyl, $(C_{1-8})$alkylthio, $(C_{1-8})$alkylthio$(C_{1-8})$alkyl, $(C_{1-8})$alkylsulfinyl, $(C_{1-8})$alkylsulfinyl$(C_{1-8})$alkyl, $(C_{1-8})$alkylsulfonyl, $(C_{1-8})$alkylsulfonyl$(C_{1-8})$alkyl, $(C_{1-8})$alkylamino, di$(C_{1-8})$alkylamino with two identical or different $(C_{1-8})$alkyl moieties, amino$(C_{1-8})$alkyl, $(C_{1-8})$alkylamino$(C_{1-8})$alkyl, di$(C_{1-8})$alkylamino$(C_{1-8})$alkyl with two identical or different $(C_{1-8})$alkyl moieties in the di$(C_{1-8})$alkylamino moiety, amino$(C_{1-8})$alkoxy, $(C_{1-8})$alkylamino$(C_{1-8})$alkoxy, di$(C_{1-8})$alkylamino$(C_{1-8})$alkoxy with two identical or different $(C_{1-8})$alkyl moieties, formyl, $(C_{1-8})$alkylcarbonyl, formyloxy, $(C_{1-8})$alkylcarbonyloxy, formyl$(C_{1-8})$alkyl, $(C_{1-8})$alkylcarbonyl$(C_{1-8})$alkyl, formyl$(C_{1-8})$alkoxy, $(C_{1-8})$alkylcarbonyl$(C_{1-8})$alkoxy, $(C_{1-8})$alkoxycarbonyl, $(C_{1-8})$alkoxycarbonyloxy, $(C_{1-8})$alkoxycarbonyl$(C_{1-8})$alkyl, $(C_{1-8})$alkoxycarbonyl$(C_{1-8})$alkoxy;

$R^4$ preferably represents hydrogen, halogen, cyano, nitro, $(C_{1-8})$alkyl, $(C_{1-8})$alkyl substituted by halogen, $(C_{3-8})$cycloalkyl, $(C_{3-8})$cycloalkyl$(C_{1-8})$alkyl, $(C_{3-8})$cycloalkoxy, $(C_{3-8})$cycloalkoxy$(C_{1-8})$alkyl, $(C_{3-8})$cycloalkyl$(C_{1-6})$alkoxy, $(C_{3-8})$cycloalkoxy$(C_{1-8})$alkoxy, aryl, aryl$(C_{1-8})$alkyl, aryloxy, aryloxy$(C_{1-8})$alkyl, aryl$(C_{1-8})$alkoxy, aryloxy$(C_{1-8})$alkoxy, carboxy, carbamyl, hydroxy, $(C_{1-8})$alkoxy, $(C_{1-8})$alkoxy$(C_{1-8})$alkoxy, $(C_{1-8})$alkoxy substituted by halogen, $(C_{1-8})$alkoxy$(C_{1-8})$alkyl, $(C_{1-8})$alkylthio, $(C_{1-8})$alkylthio$(C_{1-8})$alkyl, $(C_{1-8})$alkylsulfinyl, $(C_{1-8})$alkylsulfinyl$(C_{1-8})$alkyl, $(C_{1-8})$alkylsulfonyl, $(C_{1-8})$alkylsulfonyl$(C_{1-8})$ alkyl, amino, $(C_{1-8})$alkylamino, di$(C_{1-8})$alkylamino with two identical or different $(C_{1-8})$alkyl moieties, amino$(C_{1-8})$alkyl, $(C_{1-8})$alkylamino$(C_{1-8})$alkyl, di$(C_{1-8})$alkylamino$(C_{1-8})$alkyl with two identical or different $(C_{1-8})$alkyl moieties in the di$(C_{1-8})$alkylamino moiety, amino, $(C_{1-8})$alkoxy, $(C_{1-8})$alkylamino $(C_{1-8})$alkoxy, di$(C_{1-8})$alkylamino $(C_{1-8})$alkoxy with two identical or different $(C_{1-8})$alkyl moieties, aminosulfonyl, $(C_{1-8})$alkylaminosulfonyl, di$(C_{1-8})$alkylaminosulfonyl with two identical or different $(C_{1-8})$alkyl moieties, formyl, $(C_{1-8})$alkylcarbonyl, formyloxy, $(C_{1-8})$alkylcarbonyloxy, formyl$(C_{1-8})$alkyl, $(C_{1-8})$alkylcarbonyl$(C_{1-8})$alkyl, formyl$(C_{1-8})$alkoxy, $(C_{1-8})$alkylcarbonyl$(C_{1-8})$alkoxy, $(C_{1-8})$alkoxycarbonyl, $(C_{1-8})$alkoxycarbonyloxy, $(C_{1-8})$alkoxycarbonyl$(C_{1-8})$alkyl and $(C_{1-8})$alkoxycarbonyl$(C_{1-8})$alkoxy;

$R^5$ represents an aryl group or a $(C_3$-$C_8)$cycloalkyl group or a heterocyclyl group with 3 to 8 ring atoms or a heteroaryl group with 3 to 8 ring atoms or a $(C_1$-$C_8)$alkyl group;

wherein said aryl group, $(C_3$-$C_8)$cycloalkyl group, heteroaryl group, heterocyclyl group is unsubstituted, mono-substituted, di-substituted or tetra-substituted, the optional substituent(s) being independently selected from the group consisting of halogen, cyano, nitro, carboxy, carbamyl, hydroxy, $(C_{1-8})$alkyl, $(C_{1-8})$alkyl substituted by halogen, $(C_{3-8})$cycloalkyl, $(C_{3-8})$cycloalkyl$(C_{1-8})$alkyl, $(C_{3-8})$cycloalkoxy, $(C_{3-8})$cycloalkoxy$(C_{1-8})$alkyl, $(C_{3-8})$cycloalkyl$(C_{1-8})$alkoxy, $(C_{3-8})$cycloalkoxy$(C_{1-8})$alkoxy, aryl, aryl$(C_{1-8})$alkyl, aryloxy, aryloxy$(C_{1-8})$alkyl, aryl$(C_{1-8})$alkoxy, aryloxy$(C_{1-8})$alkoxy, $(C_{1-8})$alkoxy, $(C_{1-8})$alkoxy$(C_{1-8})$alkoxy, $(C_{1-8})$alkoxy substituted by halogen, $(C_{1-8})$alkoxy$(C_{1-8})$alkyl, $(C_{1-8})$alkylthio, $(C_{1-8})$alkylthio$(C_{1-8})$alkyl, $(C_{1-8})$alkylsulfinyl, $(C_{1-8})$alkylsulfinyl$(C_{1-8})$alkyl, $(C_{1-8})$alkylsulfonyl, $(C_{1-8})$alkylsulfonyl$(C_{1-8})$alkyl, amino, $(C_{1-8})$alkylamino, di$(C_{1-8})$alkylamino with two identical or different $(C_{1-8})$alkyl moieties, amino$(C_{1-8})$alkyl, $(C_{1-8})$alkylamino$(C_{1-8})$alkyl, di$(C_{1-8})$alkylamino$(C_{1-8})$alkyl with two identical or different $(C_{1-8})$alkyl moieties in the di$(C_{1-8})$alkylamino moiety, amino$(C_{1-8})$alkoxy, $(C_{1-8})$alkylamino$(C_{1-8})$alkoxy, di$(C_{1-8})$alkylamino$(C_{1-8})$alkoxy with two identical or different $(C_{1-8})$alkyl moieties, formyl, $(C_{1-8})$alkylcarbonyl, formyloxy, $(C_{1-8})$alkylcarbonyloxy, formyl$(C_{1-8})$alkyl, $(C_{1-8})$alkylcarbonyl$(C_{1-8})$alkyl, formyl$(C_{1-8})$alkoxy, $(C_{1-8})$alkylcarbonyl$(C_{1-8})$alkoxy, $(C_{1-8})$alkoxycarbonyl, $(C_{1-8})$alkoxycarbonyloxy, $(C_{1-8})$alkoxycarbonyl$(C_{1-8})$alkyl, $(C_{1-8})$alkoxycarbonyl$(C_{1-8})$alkoxy, —OCH$_2$O—, —C(=O)OCH$_2$—, —CH$_2$OC(=O)— and —CH=CHCH=CH—, the four last-mentioned optional substituents in each case being attached to two adjacent ring carbon atoms of the said moiety and wherein said $(C_{1-8})$alkyl group is unsubstituted or mono-, di-, tri or tetra-substituted, the optional substituent(s) on the said $(C_{1-8})$alkyl moiety being independently selected from the group consisting of halogen, cyano, oxo, $(C_{1-8})$alkoxy, $(C_{1-8})$alkoxy$(C_{1-8})$alkoxy, $(C_{1-8})$alkylthio, $(C_{1-8})$alkylsulfinyl, $(C_{1-8})$ alkylsulfonyl, $(C_{1-8})$alkylcarbonyloxy, $(C_{1-8})$alkoxycarbonyl and $(C_{1-8})$alkoxy carbonyloxy;

$R^6$ represents hydrogen, $C_1$-$C_4$ alkyl, $C_3$-$C_7$ cycloalkyl;

$R^7$ represents hydrogen, an aryl group or a $(C_3$-$C_8)$cycloalkyl group or a $(C_1$-$C_8)$alkyl group;

wherein said aryl group, $(C_3$-$C_8)$cycloalkyl group, is unsubstituted, mono-substituted, di-substituted or tetra-substituted, the optional substituent(s) being independently selected from the group consisting of halogen, cyano, nitro, carboxy, carbamyl, hydroxy, $(C_{1-8})$alkyl, $(C_{1-8})$alkyl substituted by halogen, $(C_{3-8})$cycloalkyl, $(C_{3-8})$cycloalkyl$(C_{1-8})$alkyl, $(C_{3-8})$cycloalkoxy, $(C_{3-8})$cycloalkoxy$(C_{1-8})$alkyl, $(C_{3-8})$cycloalkyl$(C_{1-8})$alkoxy, $(C_{3-8})$cycloalkoxy$(C_{1-8})$alkoxy, aryl, aryl$(C_{1-8})$alkyl, aryloxy, aryloxy$(C_{1-8})$alkyl, aryl$(C_{1-8})$alkoxy, aryloxy $(C_{1-8})$alkoxy, $(C_{1-8})$alkoxy, $(C_{1-8})$alkoxy$(C_{1-8})$alkoxy, $(C_{1-8})$alkoxy substituted by halogen, $(C_{1-8})$alkoxy$(C_{1-8})$alkyl, $(C_{1-8})$alkylthio, $(C_{1-8})$alkylthio$(C_{1-8})$alkyl, $(C_{1-8})$alkylsulfinyl, $(C_{1-8})$alkylsulfinyl$(C_{1-8})$alkyl, $(C_{1-8})$alkylsulfonyl, $(C_{1-8})$alkylsulfonyl$(C_{1-8})$alkyl, amino, $(C_{1-8})$alkylamino, di$(C_{1-8})$alkylamino with two identical or different $(C_{1-8})$alkyl moieties, amino$(C_{1-8})$alkyl, $(C_{1-8})$alkylamino$(C_{1-8})$alkyl, di$(C_{1-8})$alkylamino$(C_{1-8})$alkyl with two identical or different $(C_{1-8})$alkyl moieties in the di$(C_{1-8})$alkylamino moiety, amino$(C_{1-8})$alkoxy, $(C_8)$alkylamino$(C_{1-8})$alkoxy, di$(C_{1-8})$alkylamino$(C_{1-8})$alkoxy with two identical or different $(C_{1-8})$alkyl moieties, formyl, $(C_{1-8})$alkylcarbonyl, formyloxy, $(C_{1-8})$alkylcarbonyloxy, formyl$(C_{1-8})$alkyl, $(C_{1-8})$alkylcarbonyl$(C_{1-8})$alkyl, formyl$(C_{1-8})$alkoxy, $(C_{1-8})$alkylcarbonyl$(C_{1-8})$alkoxy, $(C_{1-8})$alkoxycarbonyl, $(C_{1-8})$alkoxycarbonyloxy, $(C_{1-8})$alkoxycarbonyl $(C_{1-8})$alkyl, $(C_{1-8})$alkoxycarbonyl$(C_{1-8})$alkoxy, —OCH$_2$—O—, —C(=O)OCH$_2$—, —CH$_2$OC(=O)— and —CH=CHCH=CH—, the four last-mentioned optional substituents in each case being attached to two adjacent ring carbon atoms of the said moiety and wherein said $(C_{1-8})$alkyl group is unsubstituted or mono-, di-, tri or tetra-substituted, the optional substituent(s) on the said $(C_{1-8})$alkyl moiety being independently selected from the group consisting of halogen, cyano, oxo, nitro, amino, $(C_{1-8})$alkoxy, $(C_{1-8})$alkoxy$(C_{1-8})$alkoxy, $(C_{1-8})$ alkylthio, $(C_{1-8})$alkylsulfinyl, $(C_{1-8})$ alkylsulfonyl, $(C_{1-8})$alkylcarbonyloxy, $(C_{1-8})$ alkoxycarbonyl and $(C_{1-8})$alkoxy carbonyloxy, $(C_{3-8})$cycloalkyl, $(C_{3-8})$cycloalkyl$(C_{1-8})$ alkyl, $(C_{3-8})$cycloalkoxy, $(C_{3-8})$cycloalkoxy$(C_{1-8})$alkyl, $(C_{3-8})$cycloalkyl$(C_{1-8})$alkoxy, $(C_{3-8})$ cycloalkoxy$(C_{1-8})$alkoxy, aryl, aryl$(C_{1-8})$alkyl, aryloxy, aryloxy$(C_{1-8})$alkyl, aryl$(C_{1-8})$alkoxy, aryloxy $(C_{1-8})$alkoxy, carboxy, carbamyl, hydroxy, $(C_{1-8})$alkoxy, $(C_{1-8})$alkoxy$(C_{1-8})$ alkoxy, $(C_{1-8})$alkoxy substituted by halogen, $(C_{1-8})$alkoxy$(C_{1-8})$alkyl, $(C_{1-8})$ alkylthio, $(C_{1-8})$ alkylthio$(C_{1-8})$alkyl, $(C_{1-8})$ alkylsulfinyl, $(C_{1-8})$alkylsulfinyl$(C_{1-8})$alkyl, $(C_{1-8})$ alkylsulfonyl, $(C_{1-8})$alkylsulfonyl$(C_{1-8})$alkyl, $(C_{1-8})$ alkylamino, di$(C_{1-8})$alkylamino with two identical or different $(C_{1-8})$alkyl moieties, amino$(C_{1-8})$alkyl, $(C_{1-8})$ alkylamino$(C_{1-8})$alkyl, di$(C_{1-8})$ alkylamino$(C_{1-8})$alkyl with two identical or different $(C_{1-8})$alkyl moieties in the di$(C_{1-8})$ alkylamino moiety, amino$(C_{1-8})$alkoxy, $(C_{1-8})$ alkylamino$(C_{1-8})$alkoxy, di$(C_{1-8})$ alkylamino$(C_{1-8})$ alkoxy with two identical or different $(C_{1-8})$alkyl moieties, formyl, $(C_{1-8})$ alkylcarbonyl, formyloxy, $(C_{1-8})$ alkylcarbonyloxy, formyl$(C_{1-8})$alkyl, $(C_{1-8})$ alkylcarbonyl$(C_{1-8})$alkyl, formyl$(C_{1-8})$alkoxy, $(C_{1-8})$ alkylcarbonyl$(C_{1-8})$alkoxy, $(C_{1-8})$ alkoxycarbonyl, $(C_{1-8})$alkoxycarbonyloxy, $(C_{1-8})$alkoxycarbonyl$(C_{1-8})$ alkyl, $(C_{1-8})$ alkoxycarbonyl$(C_{1-8})$alkoxy.

3. A process for the preparation of a compound of the formula I as defined in claim 1, in free base form or in acid addition salt form, comprising the steps of A (to obtain a compound of formula (I) wherein X represents —N(H)—C(O)—N(H)—): reacting of a compound of the formula (VI)

(VI)

wherein A represents an amino group and the remaining substituents are as defined for the formula (I), with a compound of the formula (VII-A)

$R^5$—NCO  (VII-A)

wherein $R^5$ is as defined in formula (I) or

B (to obtain a compound of formula (I) wherein X represents —C(O)N(H)—): reacting a compound of formula (VI)

(VI)

wherein A represents an amino group and the remaining substituents are as defined for the formula (I), with a compound of the formula (VII-B)

$R^5$C(O)-LG  (VII-B)

wherein $R^5$ is as defined in formula (I) and LG represents a leaving group, such as a halogen, or C (to obtain a compound of formula (I) wherein X represents —N(H)—C(O)—): reacting a compound of formula (VI)

(VI)

wherein A represents a carboxy group and the remaining substituents are as defined for the formula (I), with a compound of the formula (VII-B)

 (VII-C)

wherein $R^5$ is as defined in formula (I);

in each case:

optionally in the presence of a base, such as a hydride;

optionally in the presence of one or more diluents;

optionally followed by reduction, oxidation or functionalization reaction of the resulting compound of formula (I)

optionally followed by cleavage of protecting groups if present, optionally followed by recovering the so obtainable compound of the formula (I) in free base form or in acid addition salt form.

4. A pharmaceutical composition, comprising:
the compound of the formula I as defined in claim 1, in free form or in pharmaceutically acceptable salt form, as active ingredient, in association with a pharmaceutical carrier or diluent.

5. A combination, comprising:
a therapeutically effective amount of the compound of the formula I as defined in claim 1, in free form or in pharmaceutically acceptable salt form, and
a second drug substance, for simultaneous or sequential administration.

6. The compound according to claim 1, wherein the compound is:

N-(1,2-Dimethyl-propyl)-4-[2-(2-methyl-5-oxo-4,4-diphenyl-4,5-dihydro-imidazol-1-yl)-acetyl]-benzamide;

N-Cyclopentyl-4-[2-(2-methyl-5-oxo-4,4-diphenyl-4.5-dihydro-imidazol-1-yl)-acetyl]-benzamide;

N,N-Diethyl-4-[2-(2-methyl-5-oxo-4,4-diphenyl-4,5-dihydro-imidazol-1-yl)-acetyl]-benzamide;

2-Ethyl-N-{4-[2-(2-methyl-5-oxo-4.4-diphenyl-4.5-dihydro-imidazol-1-yl)-ethyl]-phenyl}-butyramide;

3-Methyl-N-{4-[2(2-methyl-5-oxo-4, 4-diphenyl-4, 5-dihydro-imidazol-1-yl)-ethyl]-phenyl}-butyramide;

1-(3,5-Dimethyl-isoxazol4-yl)-3-{4-[2-(2-methyl-5-oxo-4-phenyl-4-propyl-4,5-dihydro-imidazol-1-yl)-acetyl]-phenyl}-urea;

1-(3.5-dimethyl-isoxazol-4-yl)-3-(4-{2-[4-(4-fluoro-phenyl)-2-methyl-5-oxo-4-propyl-4,5-dihydroimidazol-1-yl]-acetyl}-phenyl) urea;

2-Ethyl-N-{4-[2-(2-methyl-5-oxo-4-phenyl-4-propyl-4, 5-dihydro-imidazol-1-yl)-acetyl]-phenyl}-butyramide;

2-Ethyl-N-(4-{2[4-(4-fluoro-phenyl)-2-methyl-5-oxo-4-propyl,4,5-dihydro-imidazol-1-yl-acetyl]-phenyl}-butyramide;

1-(3,5-Dimethyl-isoxazol-4-yl)-3-{3-fluoro-4-[2-(2-methyl-5-oxo-4-phenyl-4-propyl-4,5-dihydroimidazol-1-yl)-acetyl]-phenyl}-urea;

1-(3,5-Dimethyl-isoxazol-4-yl)-3-(3-fluoro-4-{2-[4-(4-fluoro-phenyl)-2-methyl-5-oxo-4-propyl-4,5-dihydro-imidazol-1-yl]acetyl)-phenyl)-urea;

2-Ethyl-N-{3-fluoro-4-[2-(2-methyl-5-oxo-4-phenyl-4-propyl-4,5-dihydro-imidazol-1-yl)-acetyl)phenyl}-butyramide;

2-Ethyl-N-(3-fluoro-4-{2-[4-{4-fluoro-phenyl)-2-methyl-5-oxo-4-propyl-4,S-dlhydro-imidazol-1-yl]acetyl rphenyl)-butyramide;

Tetrahydro-furan-3-carboxylic acid (3-fluoro-4-{2-[4-(4-fluoro-phenyl)-2-methyl-5-oxo-4-propyl-4.5-dihydro-imidazol-1-yl)-acetyl}phenyl)-amide;

Tetrahydro-furan-3-carboxylic acid {3-fluoro-4-[2-(2-methyl-5-oxo-4-phenyl-4-propyl-4,5-dihydroimidazol-1-yl)-acetyl}-phenyl)-amide;

Tetrahydro-furan-3-carboxylic acid (4-{_2-(2[4-(4-fluoro-phenyl)-2-methyl-5-oxo-4-propyl-4,5-dihydro-imidazol-1-yl]acetyl}-phenyl)-amide:

2-(3,5-Dimethyl-isoxazol-4-yl)-N-(3-fluoro-4-{2[4-(4-fluoro-phenyl)-2-methyl-5-oxo-4-propyl-4,5-dihydro-imidazol-1-yl]-acetyl}-phenyl)-acetamide;

1-(3,5-Dimethyl-isoxazol-4-yl)-3-(3-fluoro-4-{2-[4-(4-fluoro-phenyl)-2-methyl-5-oxo-4-propyl-4,5-dihydro-imidazol-1-yl]-acetyl}-phenyl)-1,3-dimethyl-urea;

2-(2,4-Dimethoxy-phenyl)-N-{4-[1-hydroxy-2-(2-methyl-5-oxo-4,4-diphenyl-4,5-dihydro-imidazol-1-yl)-ethyl]-phenyl}-acetamide;

N-{4-[1-Hydroxy-2-(2-methyl-5-oxo-4,4-diphenyl-4,5-dihydro-imidazol-1-yl)-ethyl)-phenyl}-2-(2-methoxy-phenyl)-acetamide;

2-Fluoro-N-{4[2-(2-methyl-5-oxo-4,4-diphenyl-4,5-dihydro-imidazol-1-yl)-acetyl]-phenyl}-benzamide;

N-{4-[2-(2-Methyl-5-oxo-4,4-diphenyl-4,5-dihydro-imidazol-1-yl)-acetyl]-phenyl}-2-o-tolyl-acetamide;

2-Methoxy-N-(4-[2-(2-methyl-S-oxo-4,4-diphenyl-4,5-dihydro-imidazol- 1-yl)-acetyl]-phenyl}-benzamide;

2-Ethyl-N-{4-[2-(2-methyl-5-oxo-4-phenyl-4-propyl-4, 5-dihydro-imidazol- 1-yl)-acetyl]-phenyl}-butyramide;

2-Ethyl-N-{4-[1-hydroxy-2-(2-methyl-5-oxo-4,4-diphenyl-4,5-dihydro-imidazol-1-yl)-ethyl]-phenyl)-butyramide;

1-(3,5-Dimethyl-isoxazol-4-yl)-3-{4-[2-(2-methyl-5-oxo-4,4-diphenyl-4,5-dihydro-imidazol-1-yl)-acetyl]-phenyl}-urea;

2-(2,4-Dimethoxy-phenyl)-N-{4-[2-(2-(2-methyl-5-oxo-4,4-diphenyl-4,5-dihydro-imidazol-1-yl)-acetyl]-phenyl }-acetamide;

2-(3,5-Dimethyl-isoxazol-4-yl)-N-{4-[2-(2-methyl-5-oxo-4,4-diphenyl-4,5-dihydro imidazol-1-yl)acetyl]-phenyl }-acetamide;

2-(2-Methoxy-phenyl)-N-{4-[2-(2-methyl-5-oxo-4,4-diphenyl-4,5-dihydro-imidazol-1-yl)-acetyl]-phenyl}-acetamide;

1-(2-Fluoro-phenyl)-3-{4-[2- (2-methyl-5-oxo-4,4-diphenyl-4,5-dihydro-imidazol- 1-yl)-acetyl]-phenyl}-urea;

1-{4[2-(2-Methyl-5-oxo-4,4-diphenyl-4,5-dihydro-imidazol- 1-yl)-acetyl]-phenyl}-3-(4-nitrophenyl)-urea;

2-Ethyl-N-{3-fluoro-4-[2-(2-methyl-5-oxo-4,4-diphenyl-4,5-dihydro-imidazol-1-yl)-acetyl]-phenyl}-butyramide;

2-Ethyl-N-{4-[2-(2-methyl-5-oxo-4,4-diphenyl-4,5-dihydro-imidazol-1-yl)-acetyl]-phenyl}-butyramide; and 2-(3,5-Dimethyl-isoxazol-4-yl)-N-(3-fluoro-4-{2[4-(4-fluoro-phenyl)-2-methyl-5-oxo-4-propyl-4,5-dihydro-imidazol-1-yl]-acetyl}-phenyl)-acetamide;

and pharmaceutically acceptable salts thereof.

* * * * *